US006756524B2

(12) United States Patent
Tanksley

(10) Patent No.: US 6,756,524 B2
(45) Date of Patent: Jun. 29, 2004

(54) GENE CONTROLLING FRUIT SIZE AND CELL DIVISION IN PLANTS

(75) Inventor: Steven D. Tanksley, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/898,659

(22) Filed: Jul. 3, 2001

(65) Prior Publication Data

US 2003/0024013 A1 Jan. 30, 2003

Related U.S. Application Data

(60) Provisional application No. 60/215,824, filed on Jul. 5, 2000.

(51) Int. Cl.$^7$ .......................... C12N 15/11; C12N 15/29; C12N 15/87; A01H 1/00; A01H 5/00
(52) U.S. Cl. ....................... 800/278; 800/320; 800/317; 800/323.3; 800/290; 800/298; 536/23.6; 536/23.1; 435/320.1; 435/419; 435/252.3; 435/468
(58) Field of Search ................................ 800/278, 290, 800/298, 320, 317, 317.4, 305, 314, 317.3, 320.2, 320.3, 323.3; 435/419, 468, 252.3, 320.1; 536/23.1, 23.6

(56) References Cited

U.S. PATENT DOCUMENTS

| 5,385,835 A | 1/1995 | Helentjaris et al. |
| 5,434,344 A | 7/1995 | Bennett et al. |
| 5,437,697 A | 8/1995 | Sebastian et al. |
| 5,746,023 A | 5/1998 | Hanafey et al. |

FOREIGN PATENT DOCUMENTS

| WO | WO98/42851 | * 10/1998 |
| WO | WO99/00503 | * 1/1999 |

OTHER PUBLICATIONS

Fourgoux–Nicol et al (1999, Plant Molecular Biology 40: 857–872).*
Esau 1977, Anatomy of Seed Plants, John Wiley and Sons, New York, pp. 429–451.*
Bowman et al, "Crabs Claw, a gene that regulates carpel and nectary development in Arabidopsis, encodes a novel protein with zinc finger and helix–loop–helix domains", 1999, Development vol. 126, pp2387–2396.*
Finnegan et al, "Transgene Inactiviation: Plants Fight Back", 1994, Bio/Technology vol. 12, pp. 883–887.*
Eshed et al, "Establishment of polarity in lateral organs of plants" 2001, Current Biology vol. 11, pp. 1251–1260.*
McConnell et al, "Role of Phabulosa and Phavoluta in determing radial patterning in shoots", 2001, Nature vol. 411, pp. 709–713.*
Bowie et al, "Deciphering the Message in Protein Sequences: Tolerance to amino acid substitution", 1990, Science vol. 247, pp. 1306–1310.*

Dai et al, Overexpression of Arabidopsis Hexokinase in Tomato Plants Inhibits Growth, Reduces Photosynthesis and Induces Rapid Sensescence.*
Chen et al., "Mapping of QTLs for Lycopene and Other Fruit Traits in a *Lycopersicon esculentum x L. pimpinellifolium* Cross and Comparison of QTLs Across Tomato Species," *Molecular Breeding* 5:283–299 (1999).
Khalf–Allah et al., "Relative Importance of Type s of Gene Action for Early–Yield, Total Yield and Fruit Size in Tomato," *Egyption J. Genetic. Cytol.* 1:51–60 (1972).
Rottmann et al., "1–Aminocyclopropane–1–Carboxylate Synthase in Tomato is Encoded by a Multigene Family Whose Transcription is Induced During Fruit and Floral Senescence," *J. Mol. Biol.* 222:937–961 (1991).
van Ooijen, "Accuracy of Mapping Quantitative Trait Loci in Autogamous Species," *Theor. Appl. Genet.* 84:803–811 (1992).
Grandillo et al., "Identifying the Loci Responsible for Natural Variation in Fruit Size and Shape in Tomato," *Theor. Appl. Genet.* 99:978–987 (1999).
Grandillo et al., "QTL Analysis of Horticultural Traits Differentiating the Cul tivated Tomato from the Closely Related Species *Lycopersicon pimpinellifolium,*" *Theor. Appl. Genet.* 92:935–951 (1996).
Weller, "Mapping and Analysis of Quantitative Trait Loci in Lycopersicon (tomato) with the Aid of Genetic Markers Using Approximate Maximum Likelihood Methods," *Heredity* 59:413–421 (1987).
Alpert et al., "High–Resolution Mapping and Isolation of a Yeast Artificial Chromosome Contig Containing fw2.2: A Major Fruit Weight Quantitative Trait Locus in Tomato," *Proc. Natl. Acad. Sci. USA* 93:15503–15507 (1996).
Brommonschenkel et al., "The Broad–Spectrum Tospovirus Resistance Gene Sw–5 of Tomato is a Homolog of the Root–Knot Nematode Resistance Gene Mi," *Mol. Plant Microbe Interact.* 13(10):1130–1138 (2000).
Frary et al., "fw2.2: A Quantitative Trait Locus Key to the Evolution of Tomato Fruit Size," *Science* 289(5476):85–88 (2000).
Vision et al., "Selective Mapping: A Strategy for Optimizing the Construction of High–Density Linkage Maps," *Genetics* 155(1):407–420 (2000).
Alpert et al., "fw2.2: A Major QTL Controlling Fruit Weight is Common to Both Red– and Green Fruited Tomato Species," *Theor. & Applied Genetics* 91:994–1000 (1995).

* cited by examiner

*Primary Examiner*—Elizabeth F. McElwain
*Assistant Examiner*—Stuart F. Baum
(74) *Attorney, Agent, or Firm*—Nixon Peabody LLP

(57) ABSTRACT

The present invention relates to the isolation and identification of a nucleic acid molecule which regulates fruit size and/or cell division in plants and the protein encoded by such a nucleic acid molecule. The invention also relates to an expression vector containing the encoding nucleic acid and methods whereby fruit size is reduced and/or increased and cell division is regulated by transformation of plants with the disclosed nucleic acid molecule. Host cells as well as transgenic plants and plant seeds containing the nucleic acid molecule of the present invention are also discussed.

44 Claims, 6 Drawing Sheets

GENE CONTROLLING FRUIT SIZE AND CELL DIVISION IN PLANTS

This application claims the benefit of U.S. Provisional Patent Application Serial No. 60/215,824, filed Jul. 5, 2000.

This invention was developed with government funding by the United States Department of Agriculture Grant No. 97-35300-4384; National Science Foundation Grant No. DBI-9872617; and Binational Agricultural Research and Development Fund No. US 2427-94. The U.S. Government may have certain rights.

FIELD OF THE INVENTION

The present invention relates to the identification of a gene which controls fruit size and/or cell division in plants, the proteins encoded by that gene, and uses thereof.

BACKGROUND OF THE INVENTION

In natural populations, most phenotypic variation is continuous and effected by alleles at multiple loci. Although this quantitative variation fuels evolutionary change and has been exploited in the domestication and genetic improvement of plants and animals, the identification and isolation of the genes underlying this variation has been difficult.

The most conspicuous and, perhaps, most important quantitative traits in plant agriculture are those associated with domestication (Doebley et al., "Genetic and Morphological Analysis of a Maize-Teosinte $F_2$ Population: Implications for the Origin of Maize," PNAS 87: 9888–9892 (1990)). Key adaptations to survival in the wild were dramatically modified by early humans; fruit-bearing crop plants are a prime example. Dramatic and relatively rapid changes in fruit size have accompanied the domestication of virtually all fruit-bearing crop species, including tomato, watermelon, apple, banana, grape, berries and a vast assortment of other tropical, subtropical, and temperate species (J. Smartt et al., Evolution of Crop Plants (Longman Group, United Kingdom, (1995)). These changes have benefited mankind but have often been at the expense of the plant's seed production, dispersal, and survival under natural conditions. The progenitor of domesticated tomato (Lycopersicon esculentum Mill.) most likely had fruit less than 1 cm in diameter and only a few grams in weight (Rick, C. M., "Tomato," Scientific American 239:76 (1978)). Such fruit were large enough to contain hundreds of seeds and yet small enough to be dispersed by small rodents or birds. In contrast, modern tomatoes can weigh as much as 1,000 grams and can exceed 150 cm in diameter. While it is known that the transition from small to large fruit occurred numerous times during the domestication of crop plants (J. Smartt, et al. Evolution of Crop Plants (Longman Group, United Kingdom, (1995)) and that it is quantitatively controlled (Paterson et al., "Mendelian Factors Underlying Quantitative Traits in Tomato: Comparison Across Species, Generations, and Environments," Genetics 127(1):181–97 (1991)), the molecular basis of this transition has thus far been unknown.

Using the approach of quantitative trait locus (QTL) mapping (Lander et al., "Mapping Mendelian Factors Underlying Quantitative Traits Using RFLP Linkage Maps," Genetics 121(1):185–99 (1989) published erratum appears in Genetics 136 (2):705 (1994)); Tanksley S. D., "Mapping Polygenes," Annu Rev Genet 27:205–33 (1993)), most of the loci involved in the evolution and domestication of tomato from small berries to large fruit have been genetically mapped (Grandillo et al., "Identifying the Loci Responsible for Natural Variation in Fruit Size and Shape in Tomato," Theor. Appl. Gen. 99:978 (1999)). One of these QTLs, fw2.2, appears to have been responsible for a key transition during domestication: all wild Lycopersicon species examined thus far contain small fruit alleles at this locus whereas modern cultivars have large fruit alleles (Alpert et al., "FW-2.2—A Major QTL Controlling Fruit Weight Is Common to Both Red-Fruited and Green-Fruited Tomato Species," Theor. Appl. Gen. 91: 994 (1995)). What is needed to further the current understanding of the genetic regulation of fruit size in plants is the identification of the nucleic acid sequence of the fw2.2 gene and of the protein product encoded by the cDNA of that gene.

The present invention is directed to achieving these objectives.

SUMMARY OF THE INVENTION

The present invention relates to an isolated nucleic acid molecule encoding a protein which regulates fruit size and/or cell division in plants.

The present invention also relates to an isolated protein which regulate fruit size and/or cell division in plants.

The present invention also relates to a method of regulating fruit size in plants by transforming a plant with a nucleic acid molecule of the present invention under conditions effective to regulate fruit size in the plant.

The present invention also relates to a method of regulating cell division in plants by transforming a plant with a nucleic acid molecule of the present invention under conditions effective to regulate cell division in the plant.

The present invention provides an important advance in the study of morphogenesis in plants, and provides new opportunities for understanding and utilizing natural variation. In particular, a greater understanding of the genetic regulation of fruit size and/or cell division in plants provides a means for the generation of agronomically superior crops through genetic manipulation.

BRIEF DESCRIPTION OF THE DRAWINGS

FIG. 2A shows the location of fw2.2 on tomato chromosome 2 in a cross between L. esculentum and a nearly isogenic line (NIL) containing a small introgression (grey area) from L. pennellii. FIG. 2B shows a contig of the fw2.2 candidate region, delimited by recombination events at XO31 and XO33. FIG. 2C shows a sequence analysis of the cos50 transgene.

FIGS. 4A–B show a CLUSTALW alignment of LpORFX (L. pennellii, AF261775) and LeORFX (L. esculentum, AF261774) with seven representatives of 26 matched from the Genbank Expressed Sequence Tag ("EST") and nucleotide databases and the contigs assembled from the TIGR tomato EST database. Sequences begin on FIG. 4A and continue onto FIG. 4B.

DETAILED DESCRIPTION OF THE INVENTION

Figure 1:
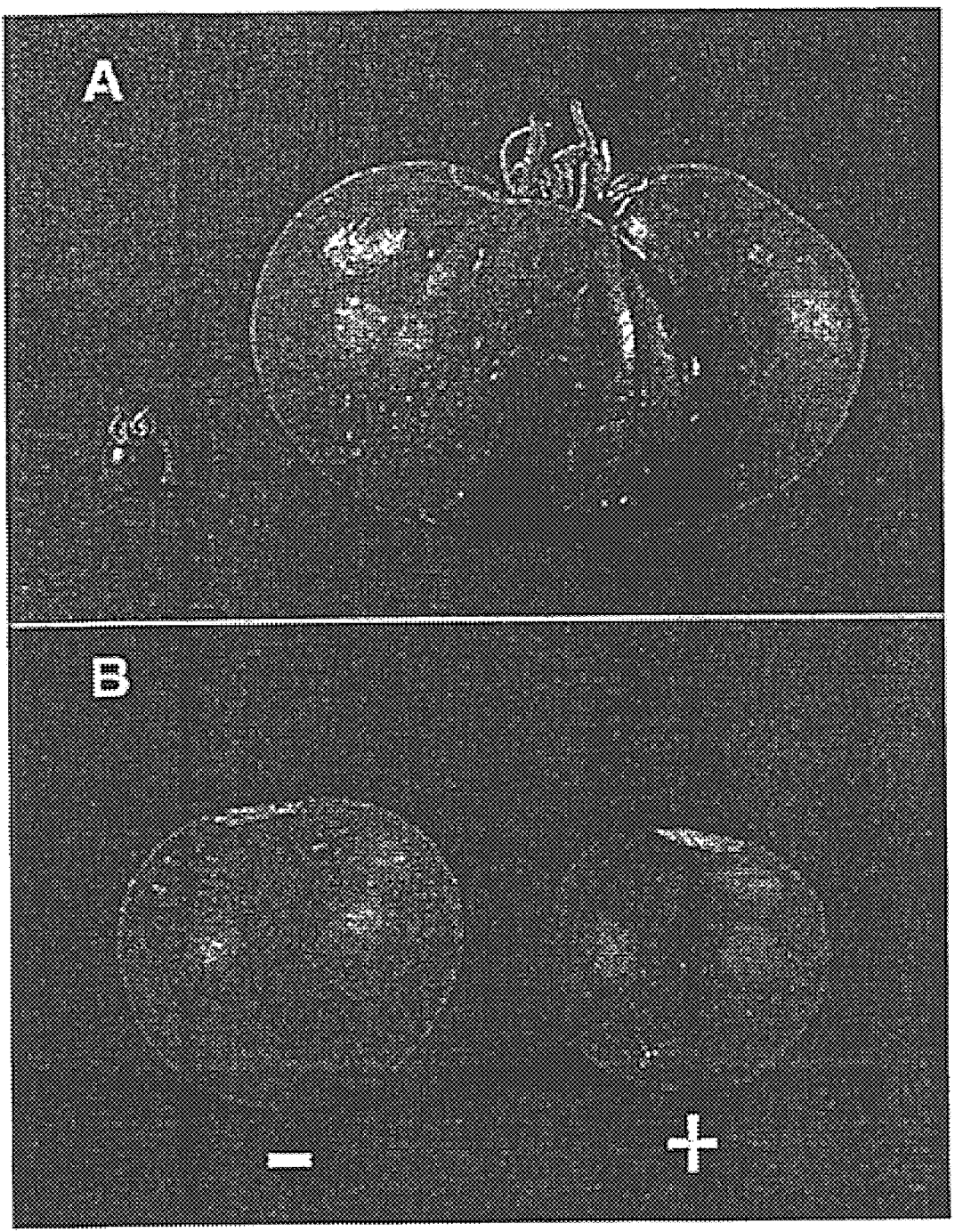
FIG. 1A shows the fruit size extremes in the genus Lycopersicon. On the left is a fruit from the wild tomato species L. pimpinellifolium, which, like all other wild tomato species, bears very small fruit. On the right is a fruit from L. esculentum cv Giant Red, bred to produce extremely large tomatoes.
FIG. 1B shows the phenotypic effect of the fw2.2 transgene in the cultivar Mogeor. Fruit are from R1 progeny of #fw107 segregating for the presence (+) and absence (−) of cos50 containing the small fruit allele.

The present invention relates to an isolated nucleic acid molecule which regulates fruit size and/or cell division in plants.

One embodiment of the nucleic acid molecule of the present invention is a nucleic acid molecule that encodes a protein which reduces fruit size and/or cell division in plants. An example of such a nucleic acid molecule is isolated from the small-fruited tomato *Lycopersicon pennellii* which has a nucleotide sequence corresponding to SEQ. ID. No. 1 as follows:

```
atgtatccaa cggtaggata taatctaggt ctaatgaaac aaccttatgt tcctcctcac   60
tatgtatctg cccccggcac caccacggcg cggtggtcaa ctggtctttg tcactgtttt  120
gatgaccctg ctaactgttt agttactagt gtttyccctt gtatcacctt tggacagatt  180
tctgaaatac taaacaaagg aacaacttca tgtgggagta gaggtgcatt atattgtttg  240
ctgggactga caggattgcc tagcctatat tcctgcttct acaggtctaa aatgaggggg  300
caatatgatc tggaagaggc accttgtgtt gattgtcttg tacatgtatt ctgtgaacct  360
tgtgctcttt gccaagaata cagagagctt aagaaccgtg gctttgatat gggaataggg  420
tggcaagcta atatggatag acaaagccgg ggagttacca tgcccccta tcatgcaggc  480 atgaccaggt ga                                                      492
```

The nucleotide sequence of SEQ. ID. No. 1 encodes a protein, LpORFX, having an amino acid sequence corresponding to SEQ. ID. No. 2, as follows:

```
Met Tyr Pro Thr Val Gly Tyr Asn Leu Gly Leu Met Lys Gln Pro Tyr
 1               5                  10                  15

Val Pro Pro His Tyr Val Ser Ala Pro Gly Thr Thr Thr Ala Arg Trp
                20                  25                  30

Ser Thr Gly Leu Cys His Cys Phe Asp Asp Pro Ala Asn Cys Leu Val
            35                  40                  45

Thr Ser Val Cys Pro Cys Ile Thr Phe Gly Gln Ile Ser Glu Ile Leu
        50                  55                  60

Asn Lys Gly Thr Thr Ser Cys Gly Ser Arg Gly Ala Leu Tyr Cys Leu
 65                 70                  75                  80

Leu Gly Leu Thr Gly Leu Pro Ser Leu Tyr Ser Cys Phe Tyr Arg Ser
                85                  90                  95

Lys Met Arg Gly Gln Tyr Asp Leu Glu Glu Ala Pro Cys Val Asp Cys
               100                 105                 110

Leu Val His Val Phe Cys Glu Pro Cys Ala Leu Cys Gln Glu Tyr Arg
           115                 120                 125

Glu Leu Lys Asn Arg Gly Phe Asp Met Gly Ile Gly Trp Gln Ala Asn
       130                 135                 140

Met Asp Arg Gln Ser Arg Gly Val Thr Met Pro Pro Tyr His Ala Gly
145                 150                 155                 160

Met Thr Arg
163
```

Another embodiment of the nucleic acid molecule of the present invention is a nucleic acid molecule that encodes a protein which increases fruit size and/or cell division in plants. An example of such a nucleic acid molecule is isolated from the large-fruited tomato *Lycopersicon esculentum* and has a nucleotide sequence corresponding to SEQ. ID. No. 3 as follows:

```
atgtatcaaa cggtaggata taatccaggt ccaatgaaac aaccttatgt tcctcctcac   60
tatgtatctg cccccggcac caccacggcg cggtggtcga ctggtctttg tcattgtttt  120
gatgaccctg ctaactgttt agttactagt gtttgccctt gtatcacctt tggacagatt  180
tctgaaatac taaacaaagg aacaacttca tgtgggagta gaggtgcatt atattgtttg  240
ctgggattga caggattgcc tagcctatat tcctgcttct acaggtctaa aatgaggggg  300
caatatgatc tggaagaggc accttgtgtt gattgtcttg tacatgtatt ctgtgaacct  360
tgtgctcttt gccaagaata cagagagctt aagaaccgtg gctttgatat gggaataggg  420
tggcaagcta atatggatag acaaagccga ggagttacca tgcccccta tcatgcaggc  480
atgaccaggt ga                                                      492
```

The nucleotide sequence of SEQ. ID. No. 3 encodes a protein, LeORFX, having an amino acid sequence corresponding to SEQ. ID. No. 4, as follows:

```
Met Tyr Gln Thr Val Gly Tyr Asn Pro Gly Pro Met Lys Gln Pro Tyr
 1               5                  10                  15
Val Pro Pro His Tyr Val Ser Ala Pro Gly Thr Thr Thr Ala Arg Trp
            20                  25                  30
Ser Thr Gly Leu Cys His Cys Phe Asp Asp Pro Ala Asn Cys Leu Val
            35                  40                  45
Thr Ser Val Cys Pro Cys Ile Thr Phe Gly Gln Ile Ser Glu Ile Leu
        50                  55                  60
Asn Lys Gly Thr Thr Ser Cys Gly Ser Arg Gly Ala Leu Tyr Cys Leu
65                  70                  75                  80
Leu Gly Leu Thr Gly Leu Pro Ser Leu Tyr Ser Cys Phe Tyr Arg Ser
                85                  90                  95
Lys Met Arg Gly Gln Tyr Asp Leu Glu Glu Ala Pro Cys Val Asp Cys
                100                 105                 110
Leu Val His Val Phe Cys Glu Pro Cys Ala Leu Cys Gln Glu Tyr Arg
            115                 120                 125
Glu Leu Lys Asn Arg Gly Phe Asp Met Gly Ile Gly Trp Gln Ala Asn
    130                 135                 140
Met Asp Arg Gln Ser Arg Gly Val Thr Met Pro Pro Tyr His Ala Gly
145                 150                 155                 160
Met Thr Arg
```

Sequence analysis of the nucleic acid molecule of the present invention, known herein as ORFX, and described in greater detail below, revealed that it contains two introns and encodes a 163 amino acid polypeptide of approximately 22 kDa. Protein secondary structure prediction algorithms (Rost et al., "Combining Evolutionary Information and Neural Networks To Predict Protein Secondary Structure," *Proteins* 19(1):55–72 (1994), which is hereby incorporated by reference in its entirety) suggest the ORFX protein has two to three hydrophobic β-strands, separated by hydrophilic turn domains, with a possible single helix near the carboxy-terminus, suggesting an overall β-sheet or mixed α-β structure. The presence of twelve highly conserved cysteine residues indicates possible zinc-finger-like domains (and thus potential interaction of the protein with DNA), but their distribution does not fit the pattern of previously characterized zinc-fingers (Struhl K., "Helix-Turn-Helix, Zinc-Finger, and Leucine-Zipper Motifs for Eukaryotic Transcriptional Regulatory Proteins," *Trends Biochem Sci* 14(4):137–40 (1989), which is hereby incorporated by reference in its entirety). The first forty amino-terminal residues are relatively hydrophilic and unstructured and are poorly conserved between putative homologs. Additional sequence analysis reveals no significant similarity to known protein motifs (BLOCKS+) (Henikoff et al., "Protein Family Classification Based On Searching A Database of Blocks," *Genomics* 1:19(1):97–107 (1994), which is hereby incorporated by reference in its entirety) or protein localization signals (PSORT) (Nakai et al., "A Knowledge Base For Predicting Protein Localization Sites in Eukaryotic Cells," *Genomics* 14(4):897–911 (1992), which is hereby incorporated by reference in its entirety).

Also suitable as a nucleic acid molecule according to the present invention is an isolated nucleic acid molecule encoding a protein which controls fruit size and/or plant cell division, wherein the nucleic acid selectively hybridizes to the nucleotide sequence of SEQ. ID. No. 1 or SEQ. ID. No. 3 under stringent conditions characterized by a hybridization buffer comprising 0.9M sodium citrate buffer at a temperature of 45° C.

Fragments of the above proteins are also encompassed by the present invention. Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein of the present invention, fragments of the gene of the present invention may be synthesized by using the PCR technique together with specific sets of primers chosen to represent particular portions of the protein. These then would be cloned into an appropriate vector for increased expression of an accessory peptide or protein.

Chemical synthesis can also be used to make suitable fragments. Such a synthesis is carried out using known amino acid sequences for the protein of the present invention. These fragments can then be separated by conventional procedures (e.g., chromatography, SDS-PAGE) and used in the methods of the present invention.

Variants may also (or alternatively) be prepared by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The present invention also relates to an expression vector containing a DNA molecule encoded by the nucleic acid molecules of the present invention. The nucleic acid molecules of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley, et al., "Expression of Bacterial Genes in Plant Cells," *Proc. Nat'l Acad. Sci.,* 80:4803–07 (1983), which is hereby incorporated by reference in its entirety).

Further improvement of this technique led to the development of the binary vector system (Bevan, M., "Binary Agrobacterium Vectors for Plant Transformation," *Nucleic Acids Res.* 12:8711–21 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch, et al., "Complete Sequence of the Binary Vector Bin19," *Plant Molec. Biol.* 27:405–409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

In one aspect of the present invention, the nucleic acid molecules of the present invention are individually incorporated into an appropriate vector in the sense direction, such that the open reading frame is properly oriented for the expression of the encoded protein under control of a promoter of choice.

Certain "control elements" or "regulatory sequences" are also incorporated into the vector-construct. These include non-translated regions of the vector, promoters, and other 5' or 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase (NOS) gene promoter, from *Agrobacterium tumefaciens* (U.S. Pat. No. 5,034,322 to Rogers et al., which is hereby incorporated by reference in its entirety), the cauliflower mosaic virus (CaMv) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci. USA* 88:10421–5 (1991), which is hereby incorporated by reference in its entirety). Expression of the protein encoded by the nucleic acid molecules of the present invention is induced in the plants transformed with the ORFX gene when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421–5 (1991); Aoyama et al., "A Glucocorticoid-Mediated Transcriptional Induction System in Transgenic Plants," *Plant J.* 11: 605–612 (1997); McNellis et al., "Glucocorticoid-Inducible Expression of a Bacterial Avirulence Gene in Transgenic Arabidopsis Induces Hypersensitive Cell Death, *Plant J.* 14(2):247–57 (1998), which are hereby incorporated by reference in their entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference in its entirety).

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA* 80:4803–07 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature* 313(6005): 810–812 (1985), which is hereby incorporated by reference in its entirety). Virtually any 3' regulatory region known to be operable in plants would suffice for proper expression of the coding sequence of the DNA construct of the present invention.

The vector of choice, promoter, and an appropriate 3' regulatory region can be ligated together to produce the plasmid, or DNA construct, of the present invention using well known molecular cloning techniques as described in Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

A further aspect of the present invention is a host cell which includes a DNA construct of the present invention. As described more fully hereinafter, the recombinant host cell can be either a bacterial cell (e.g., Agrobacterium), a virus, or a plant cell. In the case of recombinant plant cells, it is preferable that the DNA construct is stably inserted into the genome of the recombinant plant cell.

The DNA construct can be incorporated into cells using conventional recombinant DNA technology. Generally, this involves inserting the DNA construct into an expression vector or system to which it is heterologous (i.e., not normally present). As described above, the DNA construct contains the necessary elements for the transcription and translation of the heterologous DNA molecule in plant cells.

Once the DNA construct of the present invention has been prepared, it is ready to be incorporated into a host cell. Recombinant molecules can be introduced into cells via transformation, particularly transduction, conjugation, mobilization, or electroporation. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant plant cell. Basically, this method is carried out by transforming a plant cell with a DNA construct of the present invention under conditions effective to yield transcription of the DNA molecule in response to the promoter. Methods of transformation may result in transient or stable expression of the DNA under control of the promoter. Preferably, the DNA construct of the present invention is stably inserted into the genome of the recombinant plant cell as a result of the transformation, although transient expression can serve an important purpose, particularly when the plant under investigation is slow-growing.

One approach to transforming plant cells with a DNA construct of the present invention is particle bombardment (also known as biolistic transformation) of the host cell. This can be accomplished in one of several ways. The first involves propelling inert or biologically active particles at cells. This technique is disclosed in U.S. Pat. Nos. 4,945, 050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824–5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA,* 79:1859–63 (1982), which is hereby incorporated by reference in its entirety).

Stable transformants are preferable for the methods of the present invention. An appropriate method of stably introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. In one embodiment of the present invention transformants are generated using the method of Frary et al, "An Examination of Factors Affecting the Efficiency of Agrobacterium-Mediated Transformation of Tomato," *Plant Cell Reports* 16: 235 (1996), which is hereby incorporated by reference in its entirety, to transform seedling explants.

Plant tissues suitable for transformation include, but are not limited to, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO Journal* 6:3901–3907 (1987), which is hereby incorporated by reference in its entirety). GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

In order to evaluate GUS activity, several substrates are available. The most commonly used are 5 bromo-4 chloro-3 indolyl glucuronide (X-Gluc) and 4 methyl-umbelliferyl-glucuronide (MUG). The reaction with X-Gluc generates a blue color that is useful in histochemical detection of the gene activity. For quantification purposes, MUG is preferred, because the umbelliferyl radical emits fluorescence under UV stimulation, thus providing better sensitivity and easy measurement by fluorometry (Jefferson et al., "GUS Fusions: β Glucuronidase as a Sensitive and Versatile Gene Fusion Marker in Higher Plants," *EMBO Journal* 6:3901–3907 (1987), which is hereby incorporated by reference in its entirety).

Other suitable selection markers include, without limitation, markers encoding for antibiotic resistance, such as neomycin phosphotransferase II (NPT II), an antibiotic marker gene which confers kanamycin resistance (Fraley, et al., *Proc. Natl. Acad. Sci. USA,* 80:4803–4807 (1983), which is hereby incorporated by reference in its entirety) and the dhfr gene, which confers resistance to methotrexate (Bourouis et al., *EMBO J.* 2:1099–1104 (1983), which is hereby incorporated by reference in its entirety). A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures, Vol.* 1: (MacMillan Publishing Co., New York, 1983); and Vasil I. R. (ed.), *Cell Culture and Somatic Cell Genetics of Plants,* Acad. Press, Orlando, Vol. I, 1984, and Vol. III (1986), which are hereby incorporated by reference in their entirety.

It is known that practically all plants can be regenerated from cultured cells or tissues. This includes, but is not limited to, all major crop plants, such as rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane. Transgenic ornamental plants, such as *Arabidopsis thaliana,* Saintpaulia, petunia, pelargonium, poinsettia, chrysanthemum, carnation, and zinnia, can also be produced which harbor the nucleic acid molecules of the present invention.

After a DNA construct of the present invention is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

Another aspect of the present invention relates to a method of regulating fruit size in a plant. This involves transforming a host which is a plant cell with the expression vector containing a nucleic acid of the present invention, under conditions effective to regulate fruit size in the plant. This method is carried out by transforming a plant cell with a construct of the present invention. In one embodiment of this aspect, the construct of the present invention is cloned into the expression vector in proper sense orientation and correct reading frame. Transgenic plants are produced as described above, which exhibit a fruit size that is modified from its normal phenotype. The phenotypic effect is to reduce fruit size when the construct contains a nucleic acid molecule having SEQ. ID. No. 1. When a nucleic acid molecule having SEQ. ID. No. 3 is used in the construct the phenotypic effect will be to increase fruit size of the plant. Preferably, the construct of the present invention is stably inserted into the genome of the recombinant plant cell as a result of the transformation.

Another aspect of the present invention relates to a method of regulating cell division in plants. This involves transforming a plant, as described above, with the nucleic acid molecules of the present invention, under conditions effective to regulate cell division in a plant. This involves transforming a plant cell with a construct of the present invention, as describe above. This method may be carried out on a variety of plant tissues, as the regulation of cell division has numerous applications. For example, cell division in carpels (which develop in fruit), sepals, and styles may be increased or decreased relative to the native phenotype of the plant depending on whether the nucleic acid molecule corresponding to SEQ. ID. No. 1 or SEQ. ID. No. 3 of the present invention is the transgene. If transformation is carried out with the nucleic acid molecule corresponding to SEQ. ID. No. 1 of the present invention, decreased cell division will occur in the transgenic plant, with plant organs, including, but not limited to, carpels, styles, and sepals of the transgenic plant. Conversely, cell division will be increased in plants transformed with SEQ. ID. No. 3 of the present invention, producing larger organs in the plant. This method of regulating cell division can be applied to many types of plants. This includes, but is not limited to, all major crop plants, such as rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane. Ornamental plants, such as *Arabidopsis thaliana*, Saintpaulia, petunia, pelargonium, poinsettia, chrysanthemum, carnation, and zinnia, can also be used with this method of regulating cell division.

EXAMPLES

Example 1

Genetic Complementation with fw2.2

A yeast artificial chromosome (YAC) containing the QTL fw2.2 was isolated and used to screen a cDNA library constructed from the small-fruited genotype, *L pennellii* LA716. Approximately 100 positive cDNA clones were identified that represent four unique transcripts: cDNA27, cDNA38, cDNA44 and cDNA70, that were derived from genes in the fw2.2 YAC contig. The four cDNAs were then used to screen a cosmid library of *L. pennellii* genomic DNA that was constructed in the binary cosmid transformation vector TDNA 04541. For the cosmid library screen, the cDNAs were sequenced and specific primers were designed for a PCR-based screen of the pooled library. Positive pools were then plated, lifted, and probed with the corresponding cDNA. Four positive, non-overlapping cosmids (cos50, cos62, cos69, and cos84) were identified, one corresponding to each unique transcript. These four cosmid clones were assembled into a physical contig of the fw2.2 region using the Long Template PCR System, using manufacturer's directions (Boehringer Mannheim, Indianapolis, Ind.). Cosmids cos50, cos62, cos69, and cos84 were used for genetic complementation analysis in transgenic plants.

The constructs were transformed into two tomato cultivars, Mogeor (fresh market-type) and TA496 (processing-type) using the method of Frary et al., "An Examination of Factors Affecting the Efficiency of Agrobacterium-Mediated Transformation of Tomato," *Plant Cell Reports* 16: 235 (1996), which is hereby incorporated by reference in its entirety. Both tomato lines carry the partially recessive large fruit allele of fw2.2. As fw2.2 is a quantitative trait locus and the *L. pennellii* allele is only partially dominant, the primary transformants (R0), which are hemizygous for the transgene, were self-pollinated to obtain segregating R1 progeny. Putative transformants were assayed using PCR and Southern hybridization for the neomycin phosphatase II (nptII) selectable marker gene that every construct carried.

FIG. 1A shows the fruit size extremes in the genus Lycopersicon. In plants containing the transgene of the present invention, a statistically significant reduction in fruit weight indicated that the plants were carrying the small fruit allele of fw2.2 and that complementation had been achieved. This result was only observed in the R1 progeny of primary transformants #fw71 and #fw107 both of which carried cos50. FIG. 1B shows the phenotypic effect of the fw2.2 transgene in the cultivar Mogeor. Fruit are from R1 progeny of the #fw107 segregating for the presence (+) of cos50, shown on the right panel of FIG. 1B, and the absence (−) of cos50, shown in the left panel of FIG. 1B. Table 1 gives the average fruit weight and seed numbers for R1 progeny of several primary transformants. Unless otherwise noted, progeny are from independent R0 plants. Numbers in parentheses are the numbers of R1 individuals tested.

TABLE 1

| Cosmid | Cultivar | R0 plant # | Average fruit weight (g) | | | Average seed number | | |
|---|---|---|---|---|---|---|---|---|
| | | | +transgene | −transgene | P-value | +transgene | −transgene | P-value |
| 50* | TA496 | fw71 | 41.6 (18) | 56.4 (7) | <0.0001 | 32.6 (18) | 28.3 (7) | 0.40 |
| 50* | TA496 | fw71 | 47.7 (23) | 68.1 (12) | <0.0001 | 31.4 (23) | 27.4 (12) | 0.44 |
| 50 | Mogeor | fw107 | 25.4 (21) | 40.9 (7) | <0.0001 | 24.1 (21) | 28.2 (7) | 0.34 |

TABLE 1-continued

| Cosmid | Cultivar | R0 plant # | Average fruit weight (g) +transgene | Average fruit weight (g) −transgene | P-value | Average seed number +transgene | Average seed number −transgene | P-value |
| --- | --- | --- | --- | --- | --- | --- | --- | --- |
| 62 | Mogeor | fw59 | 46.5 (18) | 48.0 (9) | 0.70 | 36.1 (18) | 36.5 (9) | 0.94 |
| 62 | TA496 | fw70 | 51.0 (21) | 51.3 (3) | 0.94 | 28.3 (21) | 39.8 (3) | 0.04 |
| 69 | Mogeor | fw51 | 50.0 (14) | 51.7 (10) | 0.58 | 29.8 (14) | 34.8 (10) | 0.15 |
| 84 | Mogeor | fw95 | 49.4 (18) | 47.9 (5) | 0.71 | 33.0 (18) | 35.5 (5) | 0.62 |

*R1 progeny of the same primary transformant.

Seed number is included in the analysis, because reduced fertility, as evidenced by reduced seed per fruit, can decrease fruit size. Thus, these data show that the change in fruit size associated with cos50 is not a byproduct of reduced fertility.

The fact that the two complementing transformation events are independent and in different tomato lines (TA496 and Mogeor) indicates that the cos50 transgene functions similarly in different genetic backgrounds and genomic locations. Thus, the progeny of plants #fw71 and #fw107 show that fw2.2 is contained within cos50.

Most QTL alleles are not fully dominant or recessive (Lander et al., "Mapping Mendelian Factors Underlying Quantitative Traits Using RFLP Linkage Maps," *Genetics* 121(l):185–99 (1989), which is hereby incorporated by reference in its entirety). The small fruit *L. pennellii* allele for fw2.2 is semi-dominant to the large fruit *L. esculentum* allele (Grandillo et al., "Identifying the Loci Responsible for Natural Variation in Fruit Size and Shape in Tomato," *Theor. Appl. Gen.* 99:978 (1999), which is hereby incorporated by reference in its entirety). R2 progeny of #fw71 were used to calculate the gene action (d/a=dominance deviation/additivity; calculated as described in Grandillo et al., "Identifying the Loci Responsible for Natural Variation in Fruit Size and Shape in Tomato," *Theor. Appl. Gen.* 99:978 (1999), which is hereby incorporated by reference in its entirety) of cos50 in the transgenic plants. The transgene had a d/a of 0.51; in previous work using NILs, fw2.2 had a d/a of 0.44. This similarity of gene action is consistent with the conclusion that the cos50 transgene carries fw2.2.

Example 2 fw2.2 Corresponds to ORFX and is Expressed in Pre-Anthesis Floral Organs

Figure 2:
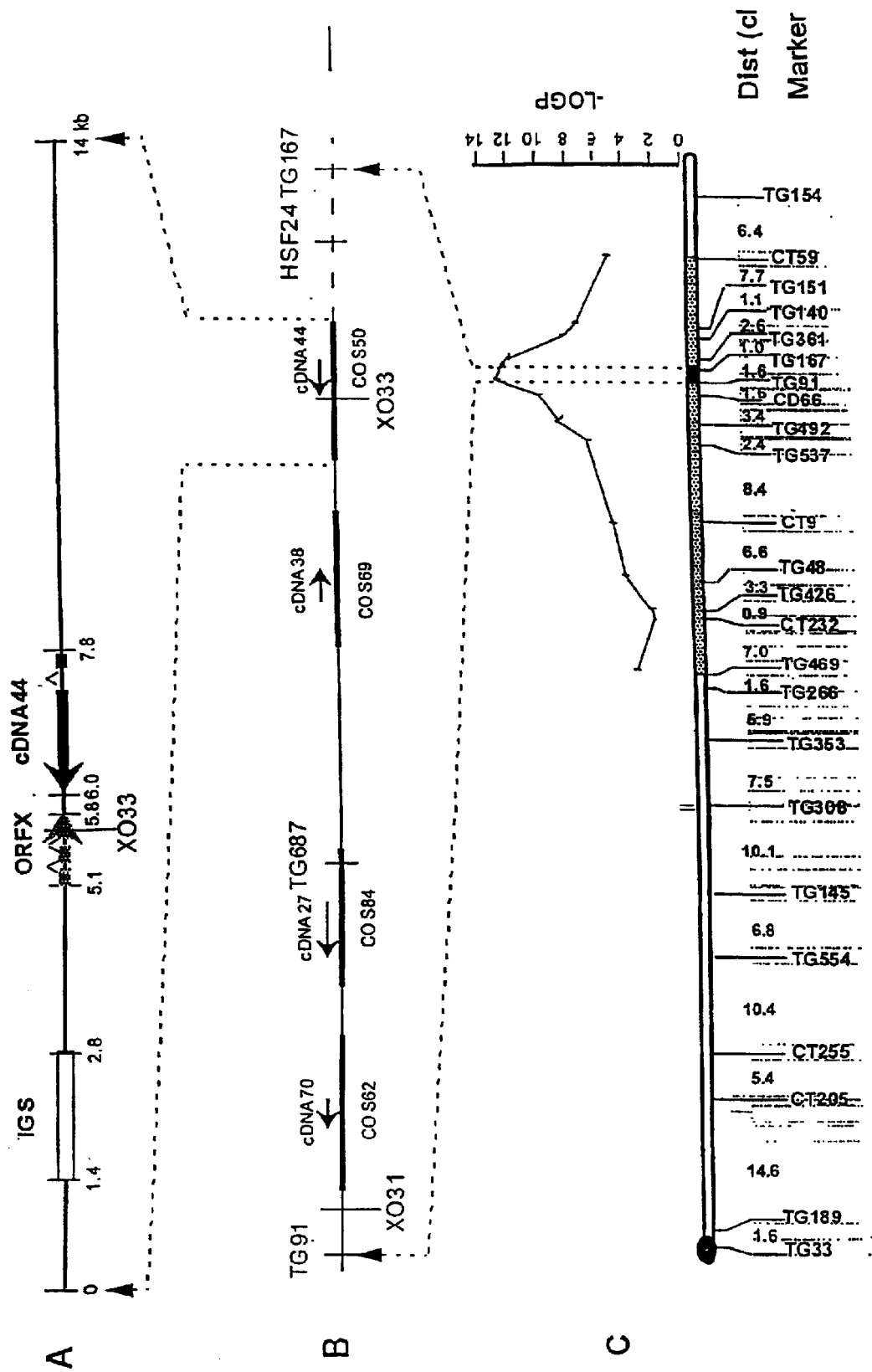
FIGS. 2A–C show the high-resolution mapping of the fw2.2 QTL.

FIG. 2A shows the location of fw2.2 on tomato chromosome 2 in a cross between *L. esculentum* and a NIL containing a small introgression (gray area) from *L. pennellii*. Sequence analysis of cos50 revealed two open reading frames ("ORF"s), shown in FIG. 2A: one corresponding to cDNA44, which was used to isolate cos50, and another 663 nucleotide (nt) gene, ORFX, for which no corresponding transcript was detected in the initial cDNA library screen. The insert also contains a highly repetitive, AT-rich (80%) region of 1.4 kb. Previous mapping of fw2.2 had identified a single recombination event which delimited the "right-most" end of the fw2.2 candidate region (XO33, as described in Alpert et al., "FW-2.2-A Major QTL Controlling Fruit Weight Is Common to Both Red-Fruited and Green-Fruited Tomato Species," *Theor. Appl. Gen.* 91: 994 (1995), which is hereby incorporated by reference in its entirety). Comparison of genomic DNA sequence from this recombinant plant with that of the two parental lines indicated that XO33 is within 43 to 80 nucleotides 5' from the end of ORFX, shown in FIG. 2A. Because genetic mutation(s) causing change in fruit size must be to the left of XO33, cDNA44 cannot be involved and ORFX or an upstream region is the likely cause of the fw2.2 QTL phenotype. FIG. 2B shows the contig of the fw2.2 candidate region, delimited by recombination events at XO31 and XO33. Arrows represent the four original candidate cDNAs (70, 27, 38, and 44, discussed in Example 1) and heavy horizontal bars are the four cosmids (cos62, 84, 69, and 50) isolated using these cDNAs as probes. The vertical lines are positions of RFLP or CAPs markers. FIG. 2C is the sequence analysis of cos50, including the positions of cDNA44, ORFX, the region showing similarity to a S-tuberosum intergenic spacer (IGS), and the "right-most" recombination event, XO33.

Figure 3:
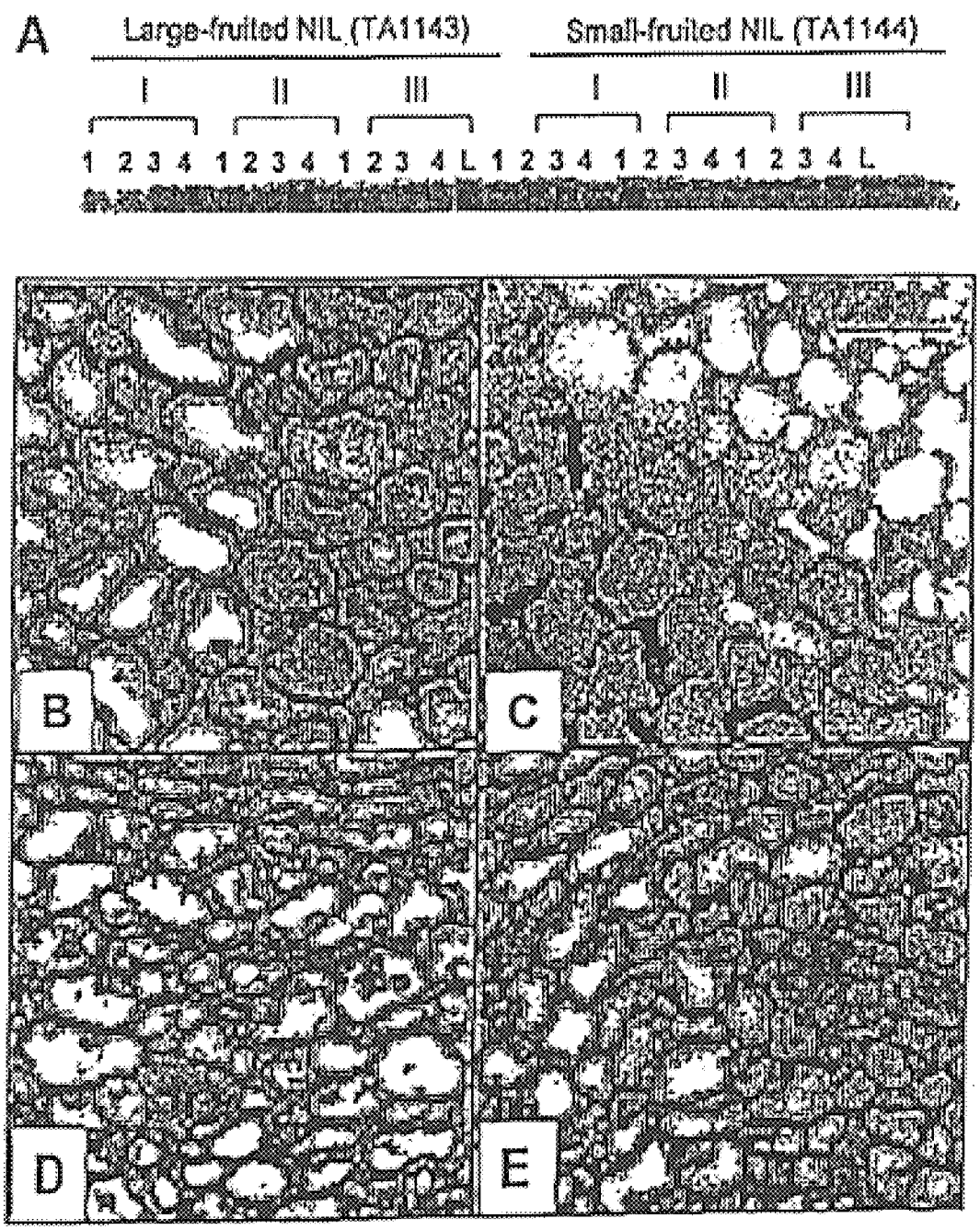
FIGS. 3A–E show the reverse transcriptase and histological analyses of the large and small-fruited NILs, TA 1143 and TA 1144, respectively.

ORFX is transcribed at levels too low to be detected through standard northern hybridization protocols in all pre-anthesis floral organs (petal, carpels, sepals, stamen) of both large and small fruited NILS; however, semi-quantitative reverse transcriptase analysis indicated that the highest levels were expressed in carpels. In addition, comparison of the relative levels of ORFX transcript in the carpels of the NILs showed significantly higher levels in the small-fruited NIL (TA1144) than in the large-fruited NIL (TA1143), as shown in FIG. 3A. FIG. 3A is a gel showing RT-PCR products for ORFX in various stages/organs. Stage I=3 to 5 mm floral buds; Stage II=5 mm to anthesis; Stage III=anthesis; 1=sepals; 2=petals; 3=stamen; 4=carpels; L=leaves. The observation of ORFX transcription in pre-anthesis carpels suggests that fw2.2 exerts its effect early in development. To test this hypothesis, a comparison was made of the floral organs from the small and large fruited NILs. The results of this comparison are shown in FIGS. 3B–E. Top sections, FIG. 3B and FIG. 3C, display cortical cells from carpel septum. Bottom sections, FIG. 3D and FIG. 3E, display pericarp cells from carpel walls. Sections on the left, FIG. 3B and FIG. 3D, were derived from carpels of NIL homozygous for large fruit allele. Sections on right, FIG. 3C and FIG. 3E, were derived from carpels of NIL homozygous for small fruit allele. Carpels (which ultimately develop into fruit), styles, and sepals of the large-fruited NIL were already significantly heavier at anthesis (p=0.0007, 0.001, and 0.001, respectively) than their counterparts in the small-fruited NIL. Stamen and petals showed no significant difference (p=0.63 and 0.74, respectively). Cell sizes at anthesis are similar (p=0.98 and p=0.85) in the NILs. Hence, carpels of large fruited genotypes contain more cells. Therefore, it was concluded that allelic variation at ORFX modulates fruit size at least in part by controlling carpel cell number prior to anthesis. TA1143 and TA1144 were not significantly different for cell size in either carpel walls (cells per $mm^2$=17,600±700 vs. 17,700±1000; p=0.98) or carpel septa (cells per $mm^2$=10,100±500 vs. 10,300±900; p=0.85) (statistical analysis based on 144 cell area counts from 48 sections). Carpels were fixed in 2.5% glutaraldehyde, 2% paraformaldehyde, 0.1 M Na cacodylate buffer, pH 6.8, and embedded in Spurr plastic. Bar represents 20 µM.

Example 3

Sequence Analysis of ORFX

Total RNA was extracted with TRIzol reagent as described by the manufacturer (Gibco BRL, Grand Island, N.Y.). First-strand cDNA was synthesized using Superscript™ RNaseH⁻ Reverse Transcriptase (Gibco BRL, Grand Island, N.Y.) with the following primers:

$B_{26}$ primer, corresponding to SEQ. ID. No. 5, as follows:

5' GACTCGAGTCGACATCGA(dT)$_{17}$ 3';

$B_{25}$ primer, corresponding to SEQ. ID. No. 6, which was used for 3' RACE PCR to amplify ORFX transcript, as follows:

5' GACTCGAGTCGACATCGA 3';

and ORFXF$_2$, corresponding to SEQ. ID. No. 7 as follows:

5' AAACAACCTTATGTTCCTCCTCA 3'.

Nested PCR was carried out using primer $B_{25}$ (SEQ. ID. No. 6) and FW01, corresponding to SEQ. ID. No. 8, as follows:

5' GCCCTTGTATCACCTTTGGA 3'.

The 5' RACE system (Gibco BRL, Grand Island, N.Y.) was employed to characterize the start of transcription of ORFX. Total RNA(5 µg) was mixed with GSP$_1$ primer corresponding to SEQ. ID. No. 9, as follows:

5' GATGATTTCATTGATCTTGCA 3' for first-strand cDNA synthesis. 5' RACE PCR was performed using an Abridged Anchor (AAP) primer (Gibco BRL, Grand Island, N.Y.), corresponding to SEQ. ID. No. 10, as follows:

5' GGCCACGCGTCGACTAGTACGGGIIGGGIIGGGIIG 3' and GSP$_2$ primer, corresponding to SEQ. ID. No. 11, as follows:

5' TAACATGAACATGCAGGGAGTC 3'.

Nested PCR was performed using an Abridged Universal Anchor primer (AUAP) (Gibco BRL, Grand Island, N.Y.), corresponding to SEQ. ID. No. 12, as follows:

5' GGCCACGCGTCGACTAGTAC 3' and GSP$_3$, corresponding to SEQ. ID. No. 13, as follows:

5' GGGAGTCGGAGATAGCATTG 3'.

After amplification, the PCR products were cloned into pCR® vector for subsequent characterization.

Example 4

Figure 4A:
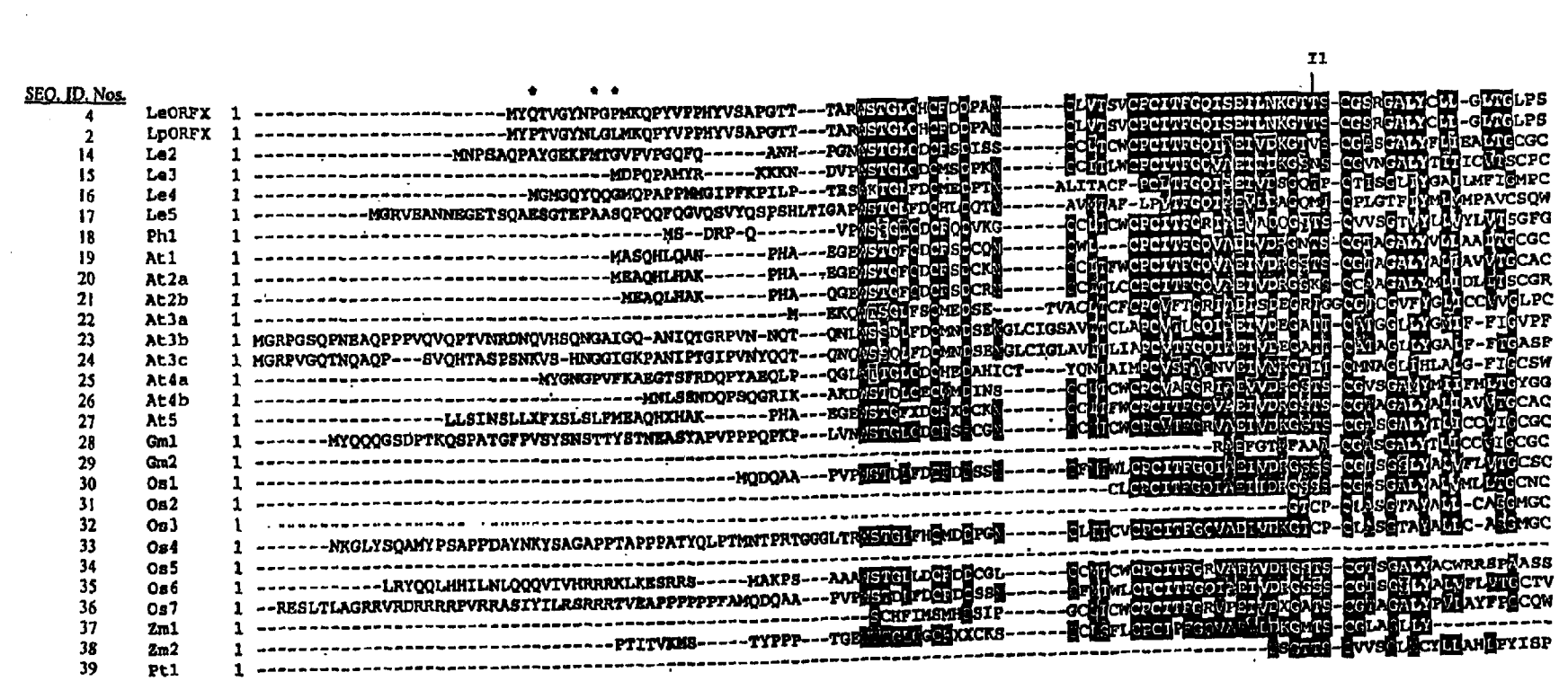
Figure 4B:
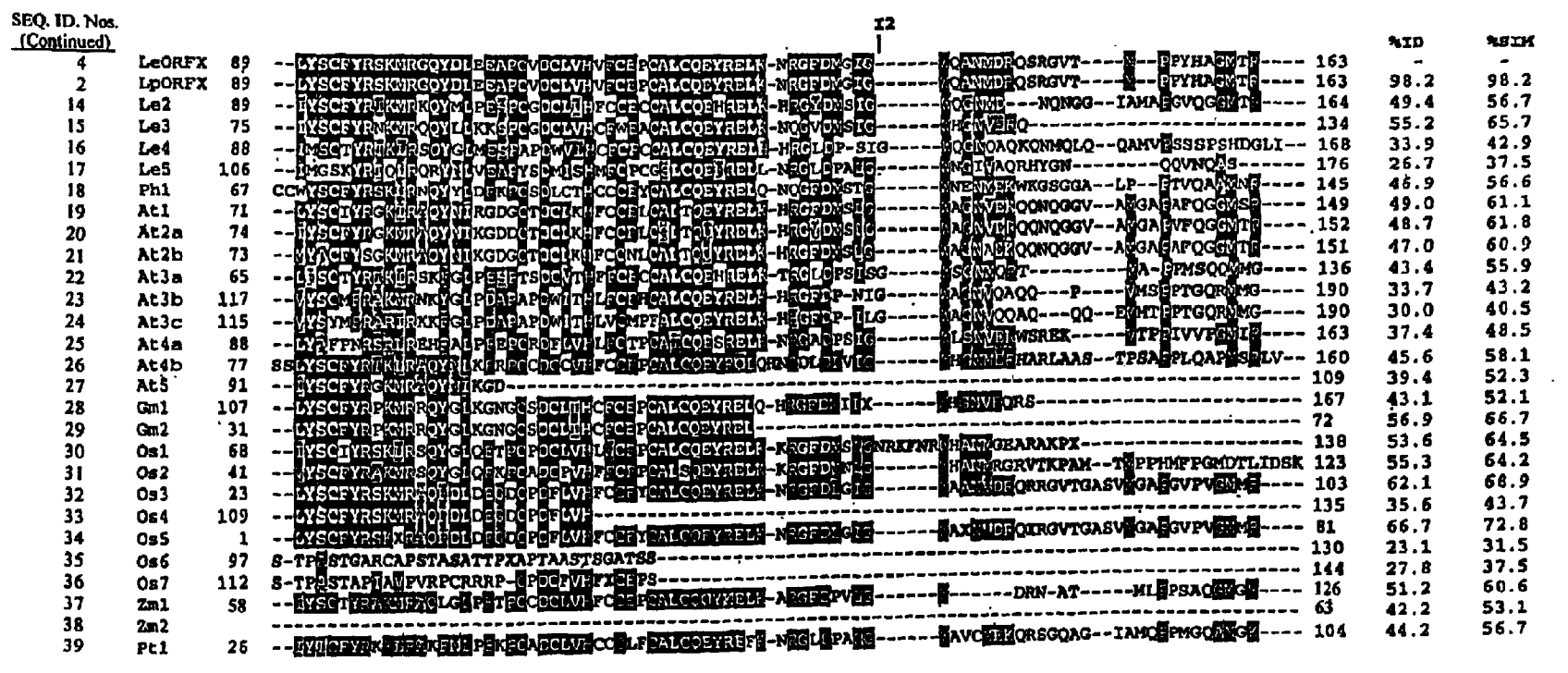

ORFX Has Homologs in Other Plant Species and Predicted Structural Similarity to Human Oncogene RAS Protein Sequence analysis of ORFX revealed that it contains two introns and encodes a 163 amino acid polypeptide of approximately 22 kD, shown in FIGS. 4A–B. Comparison of the predicted amino acid sequence of the ORFX cDNA against sequences in the Genbank EST database found matches only with plant genes. FIGS. 4A–B show a CLUSTALW alignment of LpORFX (L. pennellii, AF261775, SEQ. ID. No. 2) and LeORFX (L. esculentum, AF261774, SEQ. ID. No. 4) showing 26 matches from the Genbank EST and nucleotide databases and the contigs assembled from the TIGR tomato EST database. LpORFX (SEQ. ID. No. 2) and LeORFX (SEQ. ID. No. 4) residues are shaded black when identical to at least 73% of all the genes included in the analysis. Shading in the other genes represents residues identical (black) or similar (grey) to the black residues in LpORFX and a "–" is a space inserted by the alignment program. Percentage of identical (% ID) or similar (% SIM) amino acid residues over the length of the available sequence are noted (some ESTs may be only partial transcripts). ESTs included in the list are identified from the following plants: Petunia hybrida ((Ph), AF049928, SEQ. ID. No. 18); Glycine max ((Gm), AI960277, SEQ. ID. Nos. 28–29); O. sativa ((Os), AU068795, SEQ. ID. Nos. 30–36); Zea mays ((Zm), AI947908, SEQ. ID. Nos. 37–38); and Pinus taeda ((Pt), AI725028, SEQ. ID. No. 39). The L. esculentum EST ((Le), (SEQ. ID. No. 4)) is contig TC3457 from the TIGR EST database. "At" represents the predicted protein from various Arabidopsis thaliana genomic sequences (SEQ. ID. Nos. 19–27). The positions of the introns in ORFX are indicated as I1 and I2, and the three residue differences between LpORFX and LeORFX are denoted with asterisks.

As shown in FIGS. 4A–B, matches up to 70% similarity were found with ESTs in both monocotyledonous and dicotyledonous species. In addition, a weaker match (56.7% similarity) was found with a gymnosperm, Pinus (Pt) (SEQ. ID. No. 39). In tomato, at least four additional paralogs of ORFX were identified in the EST database. Eight homologs of ORFX appear in Arabidopsis genomic sequence, often in 2 or 3-gene clusters, and having intron-exon arrangements similar to ORFX. None of the putative homologs of ORFX has a known function. Thus, ORFX appears to represent a previously uncharacterized plant-specific multigene family.

Figure 5:
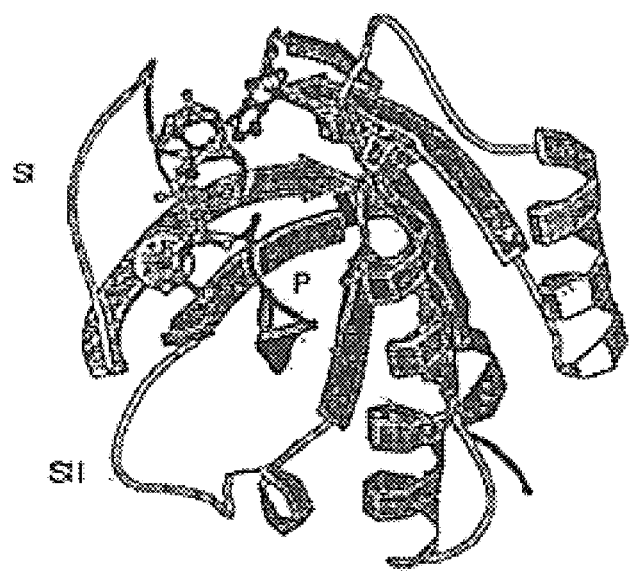
FIG. 5A shows the secondary structure analysis of the predicted ORFX protein, which indicates that ORFX is a soluble protein with α/β type secondary structure.
FIG. 5B shows the threading program LOOPP analysis which assigns ORFX to the fold of 6q21, domain A, and gives the Z-scores for global and local alignments.

Analysis of the predicted amino acid sequence indicates that ORFX is a soluble protein with α/β type secondary structure, shown in FIG. 5A. FIG. 5B shows the threading program LOOPP analysis, (predicted ORFX protein was compared to a training set of 594 structures, chosen from PDB to eliminate redundancy, using the LOOPP algorithms) assigns ORFX to the fold of 6q21, domain A, which is human oncogene RAS protein. The Z-scores for global and local alignments of ORFX are 3.2 and 4, respectively, suggesting an overall shape similar to G-proteins. The detailed comparison of ORFX sequence with that of the RAX (where X can be S, N or D) family, reveals conserved fingerprints at RAX binding domains. The RAX family includes proteins with wide regulatory functions, including control of cell division (Sprang, S. R., "G Proteins, Effectors and GAPs: Structure and Mechanism," Curr. Opin. Struct. Biol. 7:849–56 (1997), which is hereby incorporated by reference in its entirety).

Example 5

The Basis for Allelic Differences at fw2.2

In an effort to understand the basis for allelic differences at fw2.2, the L. pennellii and L. esculentum ORFX alleles were compared by amplifying and sequencing a 830 nt fragment containing ORFX (including 55 nt from the 3'UTR and 95 nt from the 5'UTR) from both NILs. Of the 42 nt differences between the two alleles, 35 fell within the two predicted introns, four represent silent mutations, and only three cause amino-acid changes. All three of the substitutions occurred within the first nine residues of the ORF, indicated as asterisks in FIG. 4A. Although the start methionine cannot be determined with certainty, if the second methionine in the ORF, shown in FIG. 5, were used, this would place all three potential substitutions in the 5' UTR. Conservation between the alleles suggests that the fw2.2 phenotype is probably not caused by differences within the coding region of ORFX, but by one or more changes upstream in the promoter region of ORFX. Variation in upstream regulatory regions of the teosinte branched1 gene has also been implicated in the domestication of maize (Wang et al., "The Limits of Selection During Maize Domestication," *Nature* 398:236–39 (1999), which is hereby incorporated by reference in its entirety). However, differences in fruit size imparted by the different fw2.2 alleles may be modulated by a combination of sequence changes in the coding and upstream regions of ORFX (Phillips, P. C., "From Complex Traits to Complex Alleles," *Trends in Genetics* 15: 6–8 (1999), which is hereby incorporated by reference in its entirety).

A reduction in cell division in carpels of the small-fruited NIL is correlated with overall higher levels of ORFX transcript, suggesting that ORFX may be a negative regulator of cell division. Whether the ORFX and RAX proteins share common properties other than predicted 3D structure and control of cell division awaits future experimentation. An affirmative result may reflect an ancient and common origin in processes of cell cycle regulation in plants and animals.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated nucleic acid molecule encoding a protein which reduces fruit size and/or cell division in plants, wherein the nucleic acid molecule either: 1) has a nucleotide sequence of SEQ. ID. No. 1 or 2) encodes a protein having an amino acid sequence of SEQ. ID. No. 2.

2. The isolated nucleic acid molecule according to claim 1, wherein the nucleic acid molecule is a plant nucleic acid molecule.

3. The isolated nucleic acid molecule according to claim 1, wherein the nucleic acid molecule has a nucleotide sequence of SEQ. ID. No. 1.

4. The isolated nucleic acid molecule according to claim 1, wherein the nucleic acid molecule encodes a protein having an amino acid sequence of SEQ. ID. No. 2.

5. An isolated nucleic acid molecule, wherein the nucleic acid molecule encodes a protein which increases fruit size and/or cell division in plants, and the nucleic acid molecule either: 1) has a nucleotide sequence of SEQ. ID. No. 3 or 2) encodes a protein having an amino acid sequence of SEQ. ID. No. 4.

6. The isolated nucleic acid molecule according to claim 5, wherein the nucleic acid molecule has a nucleotide sequence of SEQ. ID. No. 3.

7. The isolated nucleic acid molecule according to claim 5, wherein the nucleic acid molecule encodes a protein having the amino acid sequence of SEQ. ID. No. 4.

8. An expression vector comprising a transcriptional and translational regulatory DNA molecule operably linked to the nucleic acid molecule according to claim 1.

9. An expression vector according to claim 8, wherein the nucleic acid molecule is in proper sense orientation and correct reading frame.

10. A host cell transformed with the nucleic acid molecule according to claim 1.

11. The host cell according to claim 10, wherein the cell is selected from the group consisting of a bacterial cell, a yeast cell, and a plant cell.

12. The host cell according to claim 11, wherein the cell is a plant cell selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

13. The host cell according to claim 11, wherein the cell is a plant cell selected from the group consisting of *Arabidopsis thaliana*, Saintpaulia, petunia, pelargonium, poinsettia, chrysanthemum, carnation, and zinnia.

14. A transgenic plant transformed with the nucleic acid molecule according to claim 1.

15. The transgenic plant according to claim 14, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

16. The transgenic plant according to claim 14, wherein the plant is selected from the group consisting of *Arabidopsis thaliana*, Saintpaulia, petunia, pelargonium, poinsettia, chrysanthemum, carnation, and zinnia.

17. A transgenic plant seed transformed with the nucleic acid molecule according to claim 1.

18. The transgenic plant seed according to claim 17, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

19. The transgenic plant seed according to claim 17, wherein the plant is selected from the group consisting of *Arabidopsis thaliana*, Saintpaulia, petunia, pelargonium, poinsettia, chrysanthemum, carnation, and zinnia.

20. A method of decreasing fruit size in plants comprising:
transforming a plant with the nucleic acid molecule according to claim 1 under conditions effective to decrease fruit size in the plant.

21. The method according to claim 20, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

22. The method according to claim 20, wherein the plant is selected from the group consisting of *Arabidopsis thaliana*, Saintpaulia, petunia, pelargonium, poinsettia, chrysanthemum, carnation, and zinnia.

23. A method of decreasing cell division in plants comprising:
transforming a plant with the nucleic acid molecule according to claim 1 under conditions effective to decrease cell division in the plant.

24. The method according to claim 23, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

25. The method according to claim 23, wherein the plant is selected from the group consisting of *Arabidopsis thaliana*, Saintpaulia, petunia, pelargonium, poinsettia, chrysanthemum, carnation, and zinnia.

26. The isolated nucleic acid molecule according to claim 5, wherein the nucleic acid molecule is a plant nucleic acid molecule.

27. An expression vector comprising a transcriptional and translational regulatory DNA molecule operably linked to a nucleic acid molecule according to claim 5.

28. An expression vector according to claim 27, wherein the nucleic acid molecule is in proper sense orientation and correct reading frame.

29. A host cell transformed with the nucleic acid molecule according to claim 5.

30. The host cell according to claim 29, wherein the cell is selected from the group consisting of a bacterial cell, a yeast cell, and a plant cell.

31. The host cell according to claim 30, wherein the cell is a plant cell selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

32. The host cell according to claim 30, wherein the cell is a plant cell selected from the group consisting of *Arabidopsis thaliana*, Saintpaulia, petunia, pelargonium, poinsettia, chrysanthemum, carnation, and zinnia.

33. A transgenic plant transformed with the nucleic acid molecule according to claim 5.

34. The transgenic plant according to claim 33, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

35. The transgenic plant according to claim 33, wherein the plant is selected from the group consisting of *Arabidopsis thaliana*, Saintpaulia, petunia, pelargonium, poinsettia, chrysanthemum, carnation, and zinnia.

36. A transgenic plant seed transformed with the nucleic acid molecule according to claim 5.

37. The transgenic plant seed according to claim 36, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

38. The transgenic plant seed according to claim 36, wherein the plant is selected from the group consisting of *Arabidopsis thaliana*, Saintpaulia, petunia, pelargonium, poinsettia, chrysanthemum, carnation, and zinnia.

39. A method of increasing fruit size in plants comprising:
transforming the plant with the nucleic acid molecule according to claim 5 under conditions effective to increase fruit size in the plant.

40. The method according to claim 39, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

41. The method according to claim 39, wherein the plant is selected from the group consisting of *Arabidopsis thaliana*, Saintpaulia, petunia, pelargonium, poinsettia, chrysanthemum, carnation, and zinnia.

42. A method of increasing cell division in plants comprising:
transforming the plant with the nucleic acid molecule according to claim 5 under conditions effective to increase cell division in the plant.

43. The method according to claim 42, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

44. The method according to claim 42, wherein the plant is selected from the group consisting of *Arabidopsis thaliana*, Saintpaulia, petunia, pelargonium, poinsettia, chrysanthemum, carnation, and zinnia.

* * * * *

SEQUENCE LISTING

<160> NUMBER OF SEQ ID NOS: 39

<210> SEQ ID NO 1
<211> LENGTH: 492
<212> TYPE: DNA
<213> ORGANISM: Lycopersicon pennellii

<400> SEQUENCE: 1

```
atgtatccaa cggtaggata taatctaggt ctaatgaaac aaccttatgt tcctcctcac      60
tatgtatctg cccccggcac caccacggcg cggtggtcaa ctggtctttg tcactgtttt     120
gatgaccctg ctaactgttt agttactagt gtttgccctt gtatcacctt tggacagatt     180
tctgaaatac taaacaaagg aacaacttca tgtgggagta gaggtgcatt atattgtttg     240
ctgggactga caggattgcc tagcctatat tcctgcttct acaggtctaa aatgagggg     300 caatatgatc tggaagaggc accttgtgtt gattgtcttg tacatgtatt ctgtgaacct     360
tgtgctcttt gccaagaata cagagagctt aagaaccgtg gctttgatat gggaataggg     420
tggcaagcta atatggatag acaaagccgg ggagttacca tgcccccta tcatgcaggc      480 atgaccaggt ga                                                         492
```

<210> SEQ ID NO 2
<211> LENGTH: 163
<212> TYPE: PRT
<213> ORGANISM: Lycopersicon pennellii

<400> SEQUENCE: 2

```
Met Tyr Pro Thr Val Gly Tyr Asn Leu Gly Leu Met Lys Gln Pro Tyr
  1               5                  10                  15

Val Pro Pro His Tyr Val Ser Ala Pro Gly Thr Thr Thr Ala Arg Trp
             20                  25                  30

Ser Thr Gly Leu Cys His Cys Phe Asp Asp Pro Ala Asn Cys Leu Val
         35                  40                  45

Thr Ser Val Cys Pro Cys Ile Thr Phe Gly Gln Ile Ser Glu Ile Leu
     50                  55                  60

Asn Lys Gly Thr Thr Ser Cys Gly Ser Arg Gly Ala Leu Tyr Cys Leu
 65                  70                  75                  80
```

-continued

```
Leu Gly Leu Thr Gly Leu Pro Ser Leu Tyr Ser Cys Phe Tyr Arg Ser
                85                  90                  95

Lys Met Arg Gly Gln Tyr Asp Leu Glu Glu Ala Pro Cys Val Asp Cys
            100                 105                 110

Leu Val His Val Phe Cys Glu Pro Cys Ala Leu Cys Gln Glu Tyr Arg
        115                 120                 125

Glu Leu Lys Asn Arg Gly Phe Asp Met Gly Ile Gly Trp Gln Ala Asn
    130                 135                 140

Met Asp Arg Gln Ser Arg Gly Val Thr Met Pro Pro Tyr His Ala Gly
145                 150                 155                 160

Met Thr Arg
```

<210> SEQ ID NO 3
<211> LENGTH: 492
<212> TYPE: DNA
<213> ORGANISM: Lycopersicon esculentum

<400> SEQUENCE: 3

```
atgtatcaaa cggtaggata taatccaggt ccaatgaaac aaccttatgt tcctcctcac      60
tatgtatctg cccccggcac caccacggcg cggtggtcga ctggtctttg tcattgtttt     120
gatgaccctg ctaactgttt agttactagt gtttgccctt gtatcacctt tggacagatt     180
tctgaaatac taaacaaagg aacaacttca tgtgggagta gaggtgcatt atattgtttg     240
ctgggattga caggattgcc tagcctatat tcctgcttct acaggtctaa aatgaggggg     300
caatatgatc tggaagaggc accttgtgtt gattgtcttg tacatgtatt ctgtgaacct     360
tgtgctcttt gccaagaata cagagagctt aagaaccgtg gctttgatat gggaataggg     420
tggcaagcta atatggatag acaaagccga ggagttacca tgccccctta tcatgcaggc     480
atgaccaggt ga                                                         492
```

<210> SEQ ID NO 4
<211> LENGTH: 163
<212> TYPE: PRT
<213> ORGANISM: Lycopersicon esculentum

<400> SEQUENCE: 4

```
Met Tyr Gln Thr Val Gly Tyr Asn Pro Gly Met Lys Gln Pro Tyr
  1               5                  10                  15

Val Pro Pro His Tyr Val Ser Ala Pro Gly Thr Thr Ala Arg Trp
             20                  25                  30

Ser Thr Gly Leu Cys His Cys Phe Asp Asp Pro Ala Asn Cys Leu Val
         35                  40                  45

Thr Ser Val Cys Pro Cys Ile Thr Phe Gly Gln Ile Ser Glu Ile Leu
     50                  55                  60

Asn Lys Gly Thr Thr Ser Cys Gly Ser Arg Gly Ala Leu Tyr Cys Leu
 65                  70                  75                  80

Leu Gly Leu Thr Gly Leu Pro Ser Leu Tyr Ser Cys Phe Tyr Arg Ser
                85                  90                  95

Lys Met Arg Gly Gln Tyr Asp Leu Glu Glu Ala Pro Cys Val Asp Cys
            100                 105                 110

Leu Val His Val Phe Cys Glu Pro Cys Ala Leu Cys Gln Glu Tyr Arg
        115                 120                 125

Glu Leu Lys Asn Arg Gly Phe Asp Met Gly Ile Gly Trp Gln Ala Asn
    130                 135                 140

Met Asp Arg Gln Ser Arg Gly Val Thr Met Pro Pro Tyr His Ala Gly
```

```
145                 150                 155                 160
Met Thr Arg

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:  B26 Primer

<400> SEQUENCE: 5
gactcgagtc gacatcga                                                       18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:  B25 Primer

<400> SEQUENCE: 6
gactcgagtc gacatcga                                                       18

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:  ORFXF2
      Primer

<400> SEQUENCE: 7
aaacaacctt atgttcctcc tca                                                 23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  FW01
      Primer

<400> SEQUENCE: 8
gcccttgtat cacctttgga                                                     20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:  GSP1
      Primer

<400> SEQUENCE: 9
gatgatttca ttgatcttgc a                                                   21

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:  Abridged
      Anchor Primer
<221> NAME/KEY: unsure
<222> LOCATION: (24)..(35)
<223> OTHER INFORMATION: N at any position in this sequence is Inosine
```

-continued

```
<400> SEQUENCE: 10
ggccacgcgt cgactagtac gggnngggnn gggnng                                    36

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: GSP2
      Primer

<400> SEQUENCE: 11
taacatgaac atgcagggag tc                                                   22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Abridged
      Universal Anchor Primer

<400> SEQUENCE: 12
ggccacgcgt cgactagtac                                                      20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: GSP3
      Primer

<400> SEQUENCE: 13
gggagtcgga gatagcattg                                                      20

<210> SEQ ID NO 14
<211> LENGTH: 164
<212> TYPE: PRT
<213> ORGANISM: Lycopersicon esculentum2

<400> SEQUENCE: 14

Met Asn Pro Ser Ala Gln Pro Ala Tyr Gly Glu Lys Pro Met Thr Gly
  1               5                  10                  15

Val Pro Val Pro Gly Gln Phe Gln Ala Asn His Pro Gly Asn Trp Ser
                 20                  25                  30

Thr Gly Leu Cys Asp Cys Phe Ser Asp Ile Ser Ser Cys Cys Leu Thr
             35                  40                  45

Cys Trp Cys Pro Cys Ile Thr Phe Gly Gln Ile Ala Glu Ile Val Asp
         50                  55                  60

Lys Gly Thr Val Ser Cys Gly Ala Ser Gly Ala Leu Tyr Phe Leu Ile
 65                  70                  75                  80

Glu Ala Leu Thr Gly Cys Gly Cys Ile Tyr Ser Cys Phe Tyr Arg Ile
                 85                  90                  95

Lys Met Arg Lys Gln Tyr Met Leu Pro Glu Ser Pro Cys Gly Asp Cys
                100                 105                 110

Leu Leu His Phe Cys Cys Glu Cys Cys Ala Leu Cys Gln Glu His Arg
            115                 120                 125

Glu Leu Lys His Arg Gly Tyr Asp Met Ser Ile Gly Trp Gln Gly Asn
        130                 135                 140

Met Asp Asn Gln Asn Gly Gly Ile Ala Met Ala Pro Gly Val Gln Gly
```

```
145                 150                 155                 160

Gly Met Thr Arg

<210> SEQ ID NO 15
<211> LENGTH: 134
<212> TYPE: PRT
<213> ORGANISM: Lycopersicon esculentum3

<400> SEQUENCE: 15

Met Asp Pro Gln Pro Ala Met Tyr Arg Lys Lys Asn Asp Val Pro
  1               5                  10                  15

Trp Ser Thr Gly Leu Cys Asp Cys Met Ser Asp Pro Lys Asn Cys Cys
                 20                  25                  30

Ile Thr Leu Trp Cys Pro Cys Ile Thr Phe Gly Gln Val Ala Glu Ile
                 35                  40                  45

Ile Asp Lys Gly Ser Asn Ser Cys Gly Val Asn Gly Ala Leu Tyr Thr
         50                  55                  60

Ile Ile Ile Cys Val Thr Ser Cys Pro Cys Ile Tyr Ser Cys Phe Tyr
 65                  70                  75                  80

Arg Asn Lys Met Arg Gln Gln Tyr Leu Leu Lys Lys Ser Pro Cys Gly
                 85                  90                  95

Asp Cys Leu Val His Cys Phe Trp Glu Ala Cys Ala Leu Cys Gln Glu
                100                 105                 110

Tyr Arg Glu Leu Lys Asn Gln Gly Val Asp Met Ser Ile Gly Trp His
                115                 120                 125

Gly Asn Val Glu Arg Gln
                130

<210> SEQ ID NO 16
<211> LENGTH: 168
<212> TYPE: PRT
<213> ORGANISM: Lycopersicon esculentum4

<400> SEQUENCE: 16

Met Gly Met Gly Gln Tyr Gln Gln Gly Met Gln Pro Ala Pro Pro Met
  1               5                  10                  15

Met Gly Ile Pro Phe Lys Pro Ile Leu Pro Thr Glu Ser Trp Lys Thr
                 20                  25                  30

Gly Leu Phe Asp Cys Met Glu Asp Pro Thr Asn Ala Leu Ile Thr Ala
                 35                  40                  45

Cys Phe Pro Cys Leu Thr Phe Gly Gln Ile Ala Glu Ile Val Asp Ser
         50                  55                  60

Gly Gln Thr Pro Cys Thr Thr Ser Gly Leu Ile Tyr Gly Ala Ile Leu
 65                  70                  75                  80

Met Phe Ile Gly Met Pro Cys Ile Met Ser Cys Thr Tyr Arg Thr Lys
                 85                  90                  95

Leu Arg Ser Gln Tyr Gly Leu Met Glu Ser Pro Ala Pro Asp Trp Val
                100                 105                 110

Ile His Cys Phe Cys Glu Cys Cys Ala Leu Cys Gln Glu Tyr Arg Glu
                115                 120                 125

Leu His His Arg Gly Leu Asp Pro Ser Ile Gly Trp Gln Gly Asn Gln
        130                 135                 140

Ala Gln Lys Gln Asn Met Gln Leu Gln Gln Ala Met Val Pro Ser Ser
145                 150                 155                 160

Ser Pro Ser His Asp Gly Leu Ile
                165
```

<210> SEQ ID NO 17
<211> LENGTH: 175
<212> TYPE: PRT
<213> ORGANISM: Lycopersicon esculentum5

<400> SEQUENCE: 17

Met Gly Arg Val Glu Ala Asn Asn Gly Glu Thr Ser Gln Ala Glu
1               5                   10                  15

Ser Gly Thr Glu Pro Ala Ala Ser Gln Pro Gln Gln Phe Gln Gly Val
            20                  25                  30

Gln Ser Val Tyr Gln Ser Pro Ser His Leu Thr Ile Gly Ala Pro Trp
            35                  40                  45

Ser Thr Gly Leu Phe Asp Cys His Leu Asp Gln Thr Asn Ala Val Met
        50                  55                  60

Thr Ala Phe Leu Pro Val Thr Phe Gly Gln Ile Ala Glu Val Leu Asp
65                  70                  75                  80

Ala Gly Gln Met Thr Cys Pro Leu Gly Thr Phe Ile Tyr Met Leu Met
                85                  90                  95

Met Pro Ala Val Cys Ser Gln Trp Ile Met Gly Ser Lys Tyr Arg Thr
            100                 105                 110

Gln Leu Arg Gln Arg Tyr Asn Leu Val Glu Ala Pro Tyr Ser Asp Met
            115                 120                 125

Ile Ser His Met Phe Cys Pro Cys Gly Ser Leu Cys Gln Glu Phe Arg
        130                 135                 140

Glu Leu Leu Asn Arg Gly Leu Asp Pro Ala Leu Gly Trp Asn Gly Ile
145                 150                 155                 160

Val Ala Gln Arg His Tyr Gly Asn Gln Gln Val Asn Gln Ala Ser
                165                 170                 175

<210> SEQ ID NO 18
<211> LENGTH: 145
<212> TYPE: PRT
<213> ORGANISM: Petunia hybrida

<400> SEQUENCE: 18

Met Ser Asp Arg Pro Gln Val Pro Trp Ser Ser Gly Ile Cys Asp Cys
1               5                   10                  15

Phe Gln Asp Val Lys Gly Cys Cys Leu Thr Cys Trp Cys Pro Cys Ile
            20                  25                  30

Thr Phe Gly Arg Ile Ala Glu Val Ala Asp Gln Gly Ser Thr Ser Cys
            35                  40                  45

Val Val Ser Gly Thr Val Tyr Leu Leu Val Tyr Leu Val Thr Ser Gly
        50                  55                  60

Phe Gly Cys Cys Trp Tyr Ser Cys Phe Tyr Arg Ser Lys Leu Arg Asn
65                  70                  75                  80

Gln Tyr Tyr Leu Asp Glu Lys Pro Cys Ser Asp Leu Cys Thr His Cys
                85                  90                  95

Cys Cys Glu Tyr Cys Ala Leu Cys Gln Glu Tyr Arg Glu Leu Gln Asn
            100                 105                 110

Gln Gly Phe Asp Met Ser Thr Gly Trp Asn Glu Asn Met Glu Lys Trp
            115                 120                 125

Lys Gly Ser Gly Gly Ala Leu Pro Pro Thr Val Gln Ala Ala Met Asn
        130                 135                 140

Arg
145

<210> SEQ ID NO 19
<211> LENGTH: 149
<212> TYPE: PRT
<213> ORGANISM: Arabidopsis thaliana1

<400> SEQUENCE: 19

Met Ala Ser Gln His Leu Gln Ala Asn Pro His Ala Glu Gly Glu Trp
1               5                   10                  15

Ser Thr Gly Phe Cys Asp Cys Phe Ser Asp Cys Gln Asn Cys Trp Leu
            20                  25                  30

Cys Pro Cys Ile Thr Phe Gly Gln Val Ala Asp Ile Val Asp Arg Gly
        35                  40                  45

Asn Thr Ser Cys Gly Thr Ala Gly Ala Leu Tyr Val Leu Leu Ala Ala
    50                  55                  60

Ile Thr Gly Cys Gly Cys Leu Tyr Ser Cys Ile Tyr Arg Gly Lys Ile
65                  70                  75                  80

Arg Ala Gln Tyr Asn Ile Arg Gly Asp Gly Cys Thr Asp Cys Leu Lys
                85                  90                  95

His Phe Cys Cys Glu Leu Cys Ala Leu Thr Gln Glu Tyr Arg Glu Leu
            100                 105                 110

Lys His Arg Gly Phe Asp Met Ser Leu Gly Trp Ala Gly Asn Val Glu
        115                 120                 125

Lys Gln Gln Asn Gln Gly Gly Val Ala Met Gly Ala Pro Ala Phe Gln
    130                 135                 140

Gly Gly Met Ser Arg
145

<210> SEQ ID NO 20
<211> LENGTH: 152
<212> TYPE: PRT
<213> ORGANISM: Arabidopsis thaliana2a

<400> SEQUENCE: 20

Met Glu Ala Gln His Leu His Ala Lys Pro His Ala Glu Gly Glu Trp
1               5                   10                  15

Ser Thr Gly Phe Cys Asp Cys Phe Ser Asp Cys Lys Asn Cys Cys Ile
            20                  25                  30

Thr Phe Trp Cys Pro Cys Ile Thr Phe Gly Gln Val Ala Glu Ile Val
        35                  40                  45

Asp Arg Gly Ser Thr Ser Cys Gly Thr Ala Gly Ala Leu Tyr Ala Leu
    50                  55                  60

Ile Ala Val Val Thr Gly Cys Ala Cys Ile Tyr Ser Cys Phe Tyr Arg
65                  70                  75                  80

Gly Lys Met Arg Ala Gln Tyr Asn Ile Lys Gly Asp Asp Cys Thr Asp
                85                  90                  95

Cys Leu Lys His Phe Cys Cys Phe Leu Cys Ser Leu Thr Gln Gln Tyr
            100                 105                 110

Arg Glu Leu Lys His Arg Gly Tyr Asp Met Ser Leu Gly Trp Ala Gly
        115                 120                 125

Asn Val Glu Arg Gln Gln Asn Gln Gly Gly Val Ala Met Gly Ala Pro
    130                 135                 140

Val Phe Gln Gly Gly Met Thr Arg
145                 150

<210> SEQ ID NO 21

```
<211> LENGTH: 151
<212> TYPE: PRT
<213> ORGANISM: Arabidopsis thaliana2b

<400> SEQUENCE: 21

Met Glu Ala Gln Leu His Ala Lys Pro His Ala Gln Gly Glu Trp Ser
 1               5                  10                  15

Thr Gly Phe Cys Asp Cys Phe Ser Asp Cys Arg Asn Cys Cys Ile Thr
             20                  25                  30

Leu Cys Cys Pro Cys Ile Thr Phe Gly Gln Val Ala Glu Ile Val Asp
         35                  40                  45

Arg Gly Ser Lys Ser Cys Cys Ala Ala Gly Ala Leu Tyr Met Leu Ile
     50                  55                  60

Asp Leu Ile Thr Ser Cys Gly Arg Met Tyr Ala Cys Phe Tyr Ser Gly
 65                  70                  75                  80

Lys Met Arg Ala Gln Tyr Asn Ile Lys Gly Asp Gly Cys Thr Asp Cys
                 85                  90                  95

Leu Lys His Phe Cys Cys Asn Leu Cys Ala Leu Thr Gln Gln Tyr Arg
            100                 105                 110

Glu Leu Lys His Arg Gly Phe Asp Met Ser Leu Gly Trp Ala Gly Asn
        115                 120                 125

Ala Glu Lys Gln Gln Asn Gln Gly Gly Val Ala Met Gly Ala Pro Ala
    130                 135                 140

Phe Gln Gly Gly Met Thr Arg
145                 150

<210> SEQ ID NO 22
<211> LENGTH: 136
<212> TYPE: PRT
<213> ORGANISM: Arabidopsis thaliana3a

<400> SEQUENCE: 22

Met Glu Lys Gln Trp Thr Ser Gly Leu Phe Ser Cys Met Glu Asp Ser
 1               5                  10                  15

Glu Thr Val Ala Cys Leu Thr Cys Phe Cys Pro Cys Val Phe Thr Gly
             20                  25                  30

Arg Ile Ala Asp Ile Ser Asp Glu Gly Arg Thr Gly Gly Cys Gly Thr
         35                  40                  45

Cys Gly Val Phe Tyr Gly Leu Ile Cys Cys Val Val Gly Leu Pro Cys
     50                  55                  60

Leu Phe Ser Cys Thr Tyr Arg Thr Lys Ile Arg Ser Lys Phe Gly Leu
 65                  70                  75                  80

Pro Glu Ser Pro Thr Ser Asp Cys Val Thr His Phe Phe Cys Glu Cys
                 85                  90                  95

Cys Ala Leu Cys Gln Glu His Arg Glu Leu Lys Thr Arg Gly Leu Asp
            100                 105                 110

Pro Ser Ile Ser Gly Trp Ser Asn Met Gln Arg Thr Met Ala Pro
        115                 120                 125

Pro Met Ser Gln Gln Met Met Gly
    130                 135

<210> SEQ ID NO 23
<211> LENGTH: 190
<212> TYPE: PRT
<213> ORGANISM: Arabidopsis thaliana3b

<400> SEQUENCE: 23
```

```
Met Gly Arg Pro Gly Ser Gln Pro Asn Glu Ala Gln Pro Pro Val
 1               5                  10                  15

Gln Val Gln Pro Thr Val Asn Arg Asp Asn Gln Val His Ser Gln Asn
             20                  25                  30

Gly Ala Ile Gly Gln Ala Asn Ile Gln Thr Gly Arg Pro Val Asn Asn
             35                  40                  45

Gln Thr Gln Asn Leu Trp Ser Ser Asp Leu Phe Asp Cys Met Asn Asp
         50                  55                  60

Ser Glu Asn Gly Leu Cys Ile Gly Ser Ala Val Ile Thr Cys Leu Ala
 65                  70                  75                  80

Pro Cys Val Thr Leu Gly Gln Ile Ala Glu Ile Val Asp Glu Gly Ala
                 85                  90                  95

Thr Thr Cys Ala Thr Gly Gly Leu Leu Tyr Gly Met Ile Phe Phe Ile
                100                 105                 110

Gly Val Pro Phe Val Tyr Ser Cys Met Phe Arg Ala Lys Met Arg Asn
                115                 120                 125

Lys Tyr Gly Leu Pro Asp Ala Pro Ala Pro Asp Trp Ile Thr His Leu
        130                 135                 140

Phe Cys Glu His Cys Ala Leu Cys Gln Glu Tyr Arg Glu Leu Lys His
145                 150                 155                 160

Arg Gly Phe Asp Pro Asn Ile Gly Trp Ala Gly Asn Val Gln Ala Gln
                165                 170                 175

Gln Pro Val Met Ser Pro Pro Thr Gly Gln Arg Met Met Gly
            180                 185                 190

<210> SEQ ID NO 24
<211> LENGTH: 190
<212> TYPE: PRT
<213> ORGANISM: Arabidopsis thaliana3c

<400> SEQUENCE: 24

Met Gly Arg Pro Val Gly Gln Thr Asn Gln Ala Gln Pro Ser Val Gln
 1               5                  10                  15

His Thr Ala Ser Pro Ser Asn Lys Val Ser His Asn Gly Gly Ile Gly
             20                  25                  30

Lys Pro Ala Asn Ile Pro Thr Gly Ile Pro Val Asn Tyr Gln Gln Thr
             35                  40                  45

Gln Asn Gln Trp Ser Ser Gln Leu Phe Asp Cys Met Asn Asp Ser Glu
         50                  55                  60

Asn Gly Leu Cys Ile Gly Leu Ala Val Ile Thr Leu Ile Ala Pro Cys
 65                  70                  75                  80

Val Thr Phe Gly Gln Ile Ala Glu Ile Val Asp Glu Gly Ala Thr Thr
                 85                  90                  95

Cys Ala Thr Ala Gly Leu Leu Tyr Gly Ala Leu Phe Phe Thr Gly Ala
                100                 105                 110

Ser Phe Val Tyr Ser Tyr Met Phe Arg Ala Arg Ile Arg Lys Lys Phe
                115                 120                 125

Gly Leu Pro Asp Ala Pro Ala Pro Asp Trp Ile Thr His Leu Val Cys
        130                 135                 140

Met Pro Phe Ala Leu Cys Gln Glu Tyr Arg Glu Leu Lys His His Gly
145                 150                 155                 160

Phe Asp Pro Ile Leu Gly Trp Ala Gly Asn Val Gln Ala Gln Gln
                165                 170                 175

Gln Glu Met Met Thr Pro Pro Thr Gly Gln Arg Met Met Gly
            180                 185                 190
```

<210> SEQ ID NO 25
<211> LENGTH: 163
<212> TYPE: PRT
<213> ORGANISM: Arabidopsis thaliana4a

<400> SEQUENCE: 25

```
Met Tyr Gly Asn Gly Pro Val Phe Lys Ala Glu Gly Thr Ser Phe Arg
 1               5                  10                  15

Asp Gln Pro Tyr Ala Glu Gln Leu Pro Gln Gly Leu Trp Thr Thr Gly
            20                  25                  30

Leu Cys Asp Cys His Glu Asp Ala His Ile Cys Thr Tyr Gln Asn Thr
        35                  40                  45

Ala Ile Met Pro Cys Val Ser Phe Ala Gln Asn Val Glu Ile Val Asn
    50                  55                  60

Arg Gly Thr Ile Thr Cys Met Asn Ala Gly Leu Ile His Leu Ala Leu
 65                 70                  75                  80

Gly Phe Ile Gly Cys Ser Trp Leu Tyr Ala Phe Pro Asn Arg Ser Arg
                85                  90                  95

Leu Arg Glu His Phe Ala Leu Pro Glu Glu Pro Cys Arg Asp Phe Leu
            100                 105                 110

Val His Leu Phe Cys Thr Pro Cys Ala Ile Cys Gln Glu Ser Arg Glu
        115                 120                 125

Leu Lys Asn Arg Gly Ala Asp Pro Ser Ile Gly Trp Leu Ser Asn Val
    130                 135                 140

Glu Lys Trp Ser Arg Glu Lys Val Thr Pro Pro Ile Val Val Pro Gly
145                 150                 155                 160

Met Ile Arg
```

<210> SEQ ID NO 26
<211> LENGTH: 160
<212> TYPE: PRT
<213> ORGANISM: Arabidopsis thaliana4b

<400> SEQUENCE: 26

```
Met Asn Leu Ser Ser Asn Asp Gln Pro Ser Gln Gly Arg Ile Lys Ala
 1               5                  10                  15

Lys Asp Trp Ser Thr Asp Leu Cys Glu Cys Trp Met Asp Ile Asn Ser
            20                  25                  30

Cys Cys Leu Thr Cys Trp Cys Pro Cys Val Ala Phe Gly Arg Ile Ala
        35                  40                  45

Glu Val Val Asp Arg Gly Ser Thr Ser Cys Gly Val Ser Gly Ala Met
    50                  55                  60

Tyr Met Ile Ile Phe Met Leu Thr Gly Tyr Gly Gly Ser Ser Leu Tyr
 65                 70                  75                  80

Ser Cys Phe Tyr Arg Thr Lys Leu Arg Ala Gln Tyr Asn Leu Lys Glu
                85                  90                  95

Arg Pro Cys Cys Asp Cys Cys Val His Phe Cys Cys Glu Pro Cys Ala
            100                 105                 110

Leu Cys Gln Glu Tyr Arg Gln Leu Gln His Asn Arg Asp Leu Asp Leu
        115                 120                 125

Val Ile Gly Trp His Gly Asn Met Glu Arg His Ala Arg Leu Ala Ala
    130                 135                 140

Ser Thr Pro Ser Ala Pro Pro Leu Gln Ala Pro Met Ser Arg Leu Val
145                 150                 155                 160
```

<210> SEQ ID NO 27
<211> LENGTH: 108
<212> TYPE: PRT
<213> ORGANISM: Arabidopsis thaliana5
<220> FEATURE:
<221> NAME/KEY: UNSURE
<222> LOCATION: (1)..(108)
<223> OTHER INFORMATION: Xaa at any position in this sequence is unknown

<400> SEQUENCE: 27

Leu Leu Ser Ile Asn Ser Leu Leu Xaa Phe Xaa Ser Leu Ser Leu Phe
 1               5                  10                  15

Met Glu Ala Gln His Xaa His Ala Lys Pro His Ala Glu Gly Glu Trp
            20                  25                  30

Ser Thr Gly Phe Xaa Asp Cys Phe Xaa Asp Cys Lys Asn Cys Cys Ile
        35                  40                  45

Thr Phe Trp Cys Pro Cys Ile Thr Phe Gly Gln Val Ala Glu Ile Val
    50                  55                  60

Asp Arg Gly Ser Thr Ser Cys Gly Thr Ala Gly Ala Leu Tyr Ala Leu
65                  70                  75                  80

Ile Ala Val Val Thr Gly Cys Ala Cys Ile Tyr Ser Cys Phe Tyr Arg
                85                  90                  95

Gly Lys Met Arg Ala Gln Tyr Asn Ile Lys Gly Asp
            100                 105

<210> SEQ ID NO 28
<211> LENGTH: 167
<212> TYPE: PRT
<213> ORGANISM: Glycine max1
<220> FEATURE:
<221> NAME/KEY: UNSURE
<222> LOCATION: (158)
<223> OTHER INFORMATION: Xaa at position 158 in this sequence is unknown

<400> SEQUENCE: 28

Met Tyr Gln Gln Gly Ser Asp Pro Thr Lys Gln Ser Pro Ala Thr
 1               5                  10                  15

Gly Phe Pro Val Ser Tyr Ser Asn Ser Thr Thr Tyr Ser Thr Asn Glu
            20                  25                  30

Ala Ser Tyr Ala Pro Val Pro Pro Gln Pro Lys Pro Leu Val Asn
        35                  40                  45

Trp Ser Thr Gly Leu Cys Asp Cys Phe Ser Glu Cys Gly Asn Cys Cys
    50                  55                  60

Met Thr Cys Trp Cys Pro Cys Val Thr Phe Gly Arg Val Ala Glu Ile
65                  70                  75                  80

Val Asp Lys Gly Ser Thr Ser Cys Gly Ala Ser Gly Ala Leu Tyr Thr
                85                  90                  95

Leu Ile Cys Cys Val Ile Gly Cys Gly Cys Leu Tyr Ser Cys Phe Tyr
            100                 105                 110

Arg Pro Lys Met Arg Arg Gln Tyr Gly Leu Lys Gly Asn Gly Cys Ser
        115                 120                 125

Asp Cys Leu Ile His Cys Phe Cys Glu Pro Cys Ala Leu Cys Gln Glu
    130                 135                 140

Tyr Arg Glu Leu Gln His Arg Gly Phe Asp Met Ile Ile Xaa Trp His
145                 150                 155                 160

Gly Asn Val Glu Gln Arg Ser
                165

```
<210> SEQ ID NO 29
<211> LENGTH: 72
<212> TYPE: PRT
<213> ORGANISM: Glycine max2

<400> SEQUENCE: 29

Arg Ala Glu Phe Gly Thr Arg Phe Ala Ala Cys Gly Ala Ser Gly
 1               5                  10                  15

Ala Leu Tyr Thr Leu Ile Cys Cys Val Ile Gly Cys Gly Cys Leu Tyr
            20                  25                  30

Ser Cys Phe Tyr Arg Pro Lys Met Arg Arg Gln Tyr Gly Leu Lys Gly
        35                  40                  45

Asn Gly Cys Ser Asp Cys Leu Ile His Cys Phe Cys Glu Pro Cys Ala
    50                  55                  60

Leu Cys Gln Glu Tyr Arg Glu Leu
65                  70

<210> SEQ ID NO 30
<211> LENGTH: 138
<212> TYPE: PRT
<213> ORGANISM: O.sativa1
<220> FEATURE:
<221> NAME/KEY: UNSURE
<222> LOCATION: (138)
<223> OTHER INFORMATION: Xaa at position 138 in this sequence is unknown

<400> SEQUENCE: 30

Met Gln Asp Gln Ala Ala Pro Val Pro Trp Ser Thr Asp Leu Phe Asp
 1               5                  10                  15

Cys Phe Asp Asp Ser Ser Asn Cys Phe Met Thr Trp Leu Cys Pro Cys
            20                  25                  30

Ile Thr Phe Gly Gln Ile Ala Glu Ile Val Asp Arg Gly Ser Ser Ser
        35                  40                  45

Cys Gly Thr Ser Gly Ser Leu Tyr Ala Leu Val Phe Leu Val Thr Gly
    50                  55                  60

Cys Ser Cys Ile Tyr Ser Cys Ile Tyr Arg Ser Lys Leu Arg Ser Gln
65                  70                  75                  80

Tyr Gly Leu Gln Glu Thr Pro Cys Pro Asp Cys Leu Val His Leu Trp
                85                  90                  95

Cys Glu Pro Cys Ala Leu Cys Gln Glu Tyr Arg Glu Leu Lys Lys Arg
            100                 105                 110

Gly Phe Asp Met Ser Leu Gly Asn Arg Lys Phe Asn Arg Trp His Ala
        115                 120                 125

Asn Met Gly Glu Ala Arg Ala Lys Pro Xaa
    130                 135

<210> SEQ ID NO 31
<211> LENGTH: 123
<212> TYPE: PRT
<213> ORGANISM: O.sativa2

<400> SEQUENCE: 31

Cys Leu Cys Pro Cys Ile Thr Phe Gly Gln Ile Ala Glu Ile Ile Asp
 1               5                  10                  15

Arg Gly Ser Ser Ser Cys Gly Thr Ser Gly Ala Leu Tyr Ala Leu Val
            20                  25                  30

Met Leu Leu Thr Gly Cys Asn Cys Val Tyr Ser Cys Phe Tyr Arg Ala
        35                  40                  45

Lys Met Arg Ser Gln Tyr Gly Leu Gln Glu Lys Pro Cys Ala Asp Cys
```

```
                 50                  55                  60
Pro Val His Phe Cys Glu Pro Cys Ala Leu Ser Gln Glu Tyr Arg
 65                  70                  75                  80

Glu Leu Lys Lys Arg Gly Phe Asp Met Asn Leu Gly Trp His Ala Asn
                 85                  90                  95

Met Arg Gly Arg Val Thr Lys Pro Ala Met Thr Met Pro Pro His Met
                100                 105                 110

Phe Pro Gly Met Asp Thr Leu Ile Asp Ser Lys
            115                 120

<210> SEQ ID NO 32
<211> LENGTH: 103
<212> TYPE: PRT
<213> ORGANISM: O.sativa3

<400> SEQUENCE: 32

Gly Thr Cys Pro Cys Leu Ala Ser Gly Thr Ala Tyr Ala Leu Leu Cys
  1               5                  10                  15

Ala Ser Gly Met Gly Cys Leu Tyr Ser Cys Phe Tyr Arg Ser Lys Met
                 20                  25                  30

Arg Ala Gln Phe Asp Leu Asp Glu Gly Asp Cys Pro Asp Phe Leu Val
             35                  40                  45

His Phe Cys Cys Glu Tyr Cys Ala Leu Cys Gln Glu Tyr Arg Glu Leu
         50                  55                  60

Lys Asn Arg Gly Phe Asp Leu Gly Ile Gly Trp Ala Ala Asn Val Asp
 65                  70                  75                  80

Arg Gln Arg Arg Gly Val Thr Gly Ala Ser Val Met Gly Ala Pro Gly
                 85                  90                  95

Val Pro Val Gly Met Met Arg
            100

<210> SEQ ID NO 33
<211> LENGTH: 135
<212> TYPE: PRT
<213> ORGANISM: O.sativa4

<400> SEQUENCE: 33

Asn Lys Gly Leu Tyr Ser Gln Ala Met Tyr Pro Ser Ala Pro Pro Asp
  1               5                  10                  15

Ala Tyr Asn Lys Tyr Ser Ala Gly Ala Pro Thr Ala Pro Pro
                 20                  25                  30

Ala Thr Tyr Gln Leu Pro Thr Met Asn Thr Pro Arg Thr Gly Gly Gly
             35                  40                  45

Leu Thr Arg Trp Ser Thr Gly Leu Phe His Cys Met Asp Asp Pro Gly
 50                  55                  60

Asn Cys Leu Ile Thr Cys Val Cys Pro Cys Ile Thr Phe Gly Gln Val
 65                  70                  75                  80

Ala Asp Ile Val Asp Lys Gly Thr Cys Pro Cys Leu Ala Ser Gly Thr
                 85                  90                  95

Ala Tyr Ala Leu Leu Cys Ala Ser Gly Met Gly Cys Leu Tyr Ser Cys
                100                 105                 110

Phe Tyr Arg Ser Lys Met Arg Ala Gln Phe Asp Leu Asp Glu Gly Asp
            115                 120                 125

Cys Pro Asp Phe Leu Val His
        130                 135
```

<210> SEQ ID NO 34
<211> LENGTH: 81
<212> TYPE: PRT
<213> ORGANISM: O.sativa5
<220> FEATURE:
<221> NAME/KEY: UNSURE
<222> LOCATION: (10)..(61)
<223> OTHER INFORMATION: Xaa at any position in this sequence is unknown

<400> SEQUENCE: 34

Leu Tyr Ser Cys Phe Tyr Arg Ser Lys Xaa Arg Ala Gln Phe Asp Leu
 1               5                  10                  15

Asp Glu Gly Asp Cys Pro Asp Phe Leu Val His Phe Cys Cys Glu Tyr
            20                  25                  30

Cys Ala Leu Cys Gln Glu Tyr Arg Glu Leu Lys Asn Arg Gly Phe Asp
        35                  40                  45

Leu Gly Ile Gly Trp Ala Xaa Asn Val Asp Arg Gln Xaa Arg Gly Val
    50                  55                  60

Thr Gly Ala Ser Val Met Gly Ala Pro Gly Val Pro Val Gly Met Met
65                  70                  75                  80

Arg

<210> SEQ ID NO 35
<211> LENGTH: 130
<212> TYPE: PRT
<213> ORGANISM: O.sativa6
<220> FEATURE:
<221> NAME/KEY: UNSURE
<222> LOCATION: (117)
<223> OTHER INFORMATION: Xaa at position 117 in this sequence is unknown

<400> SEQUENCE: 35

Leu Arg Tyr Gln Gln Leu His His Ile Leu Asn Leu Gln Gln Gln Val
 1               5                  10                  15

Ile Val His Arg Arg Lys Leu Lys Glu Ser Arg Arg Ser Met Ala
            20                  25                  30

Lys Pro Ser Ala Ala Ala Trp Ser Thr Gly Leu Leu Asp Cys Phe Asp
        35                  40                  45

Asp Cys Gly Leu Cys Cys Met Thr Cys Trp Cys Pro Cys Ile Thr Phe
    50                  55                  60

Gly Arg Val Ala Glu Met Val Asp Arg Gly Ser Thr Ser Cys Gly Thr
65                  70                  75                  80

Ser Gly Ala Leu Tyr Ala Cys Trp Arg Arg Ser Pro Ala Ala Ser Ser
                85                  90                  95

Ser Thr Pro Ala Ser Thr Gly Ala Arg Cys Ala Pro Ser Thr Ala Ser
            100                 105                 110

Ala Thr Thr Pro Xaa Ala Pro Thr Ala Ala Ser Thr Ser Gly Ala Thr
        115                 120                 125

Ser Ser
    130

<210> SEQ ID NO 36
<211> LENGTH: 144
<212> TYPE: PRT
<213> ORGANISM: O.sativa7
<220> FEATURE:
<221> NAME/KEY: UNSURE
<222> LOCATION: (140)
<223> OTHER INFORMATION: Xaa at position 140 in this sequence is unknown

<400> SEQUENCE: 36

```
Arg Glu Ser Leu Thr Leu Ala Gly Arg Arg Val Arg Asp Arg Arg
  1               5                  10                  15

Arg Pro Val Arg Arg Ala Ser Ile Tyr Ile Leu Arg Ser Arg Arg
             20                  25                  30

Thr Val Glu Ala Pro Pro Pro Pro Phe Ala Met Gln Asp Gln
         35                  40                  45

Ala Ala Pro Val Pro Trp Ser Thr Asp Leu Phe Asp Cys Phe Asp Asp
 50                  55                  60

Ser Ser Asn Cys Phe Met Thr Trp Leu Cys Pro Cys Ile Thr Phe Gly
 65                  70                  75                  80

Gln Ile Ala Glu Ile Val Asp Arg Gly Ser Ser Cys Gly Thr Ser
                 85                  90                  95

Gly Ser Leu Tyr Ala Leu Val Phe Leu Val Thr Gly Cys Thr Val Ser
                100                 105                 110

Thr Pro Ala Ser Thr Ala Pro Thr Ala Val Pro Val Arg Pro Cys Arg
                115                 120                 125

Arg Arg Pro Cys Pro Asp Cys Phe Val His Phe Xaa Cys Glu Pro Ser
130                 135                 140
```

```
<210> SEQ ID NO 37
<211> LENGTH: 126
<212> TYPE: PRT
<213> ORGANISM: Zea mays1
<220> FEATURE:
<221> NAME/KEY: UNSURE
<222> LOCATION: (34)
<223> OTHER INFORMATION: Xaa at position 34 in this sequence is unknown

<400> SEQUENCE: 37
```

```
Ser Cys His Phe Ile Met Ser Met His Asp Ser Ile Pro Gly Cys Leu
  1               5                  10                  15

Thr Cys Trp Cys Pro Cys Ile Thr Phe Gly Arg Val Pro Glu Ile Val
             20                  25                  30

Asp Xaa Gly Ala Thr Ser Cys Gly Thr Ala Gly Ala Leu Tyr Pro Val
         35                  40                  45

Leu Ala Tyr Phe Pro Gly Cys Gln Trp Ile Tyr Ser Cys Thr Tyr Arg
 50                  55                  60

Ala Lys Met Arg Ala Gln Leu Gly Leu Pro Glu Thr Pro Cys Cys Asp
 65                  70                  75                  80

Cys Leu Val His Phe Cys Glu Pro Cys Ala Leu Cys Gln Gln Tyr
                 85                  90                  95

Lys Glu Leu Lys Ala Arg Gly Phe Asp Pro Val Leu Gly Trp Asp Arg
                100                 105                 110

Asn Ala Thr Met Leu Pro Pro Ser Ala Gln Gly Met Gly Arg
                115                 120                 125
```

```
<210> SEQ ID NO 38
<211> LENGTH: 63
<212> TYPE: PRT
<213> ORGANISM: Zea mays2
<220> FEATURE:
<221> NAME/KEY: UNSURE
<222> LOCATION: (26)..(27)
<223> OTHER INFORMATION: Xaa at positions 26 and 27 are unknown

<400> SEQUENCE: 38
```

```
Pro Thr Ile Thr Val Lys Met Ser Thr Tyr Pro Pro Pro Thr Gly Glu
  1               5                  10                  15

Trp Thr Thr Gly Leu Cys Gly Cys Phe Xaa Xaa Cys Lys Ser Cys Cys
```

-continued

```
                 20                  25                  30
Leu Ser Phe Leu Cys Pro Cys Ile Pro Phe Gly Gln Val Ala Glu Val
             35                  40                  45

Leu Asp Lys Gly Met Thr Ser Cys Gly Leu Ala Gly Leu Leu Tyr
         50                  55                  60

<210> SEQ ID NO 39
<211> LENGTH: 104
<212> TYPE: PRT
<213> ORGANISM: Pinus taeda

<400> SEQUENCE: 39

Asp Ser Gly Thr Thr Ser Cys Val Val Ser Gly Leu Met Cys Tyr Leu
 1               5                  10                  15

Leu Ala His Leu Pro Tyr Ile Ser Pro Ile Tyr Ile Cys Phe Tyr Arg
             20                  25                  30

Lys Lys Leu Arg Ala Lys Phe Asn Leu Pro Glu Lys Pro Cys Ala Asp
             35                  40                  45

Cys Leu Val His Cys Cys Cys Leu Phe Cys Ala Leu Cys Gln Glu Tyr
         50                  55                  60

Arg Glu Phe Lys Asn Arg Gly Leu Asp Pro Ala Leu Gly Trp Ala Val
65                  70                  75                  80

Cys Met Glu Lys Gln Arg Ser Gly Gln Ala Gly Ile Ala Met Gln Pro
             85                  90                  95

Pro Met Gly Gln Ala Met Gly Lys
                100
```